(12) United States Patent
Hartwell

(10) Patent No.: US 11,439,741 B2
(45) Date of Patent: Sep. 13, 2022

(54) FLUIDIC CONNECTOR FOR IRRIGATION AND ASPIRATION OF WOUNDS

(71) Applicant: Smith & Nephew PLC, Watford (GB)

(72) Inventor: Edward Yerbury Hartwell, Hull (GB)

(73) Assignee: Smith & Nephew PLC, Watford (GB)

( * ) Notice: Subject to any disclaimer, the term of this patent is extended or adjusted under 35 U.S.C. 154(b) by 860 days.

(21) Appl. No.: 16/025,871

(22) Filed: Jul. 2, 2018

(65) Prior Publication Data

US 2018/0311418 A1    Nov. 1, 2018

Related U.S. Application Data

(62) Division of application No. 14/889,825, filed as application No. PCT/IB2014/001682 on May 6, 2014, now Pat. No. 10,010,658.

(Continued)

(51) Int. Cl.
*A61M 1/00* (2006.01)
*A61F 13/00* (2006.01)
(Continued)

(52) U.S. Cl.
CPC ......... *A61M 1/86* (2021.05); *A61F 13/00068* (2013.01); *A61M 1/85* (2021.05);
(Continued)

(58) Field of Classification Search
CPC .............. A61M 1/0086; A61M 3/0279; A61M 39/105; A61M 1/0084; A61M 1/0088;
(Continued)

(56) References Cited

U.S. PATENT DOCUMENTS 3,171,410 A    3/1965  Towle et al.
3,288,140 A    11/1966 McCarthy
(Continued)

FOREIGN PATENT DOCUMENTS

AU    674837       1/1997
CN    202069996    12/2011
(Continued)

OTHER PUBLICATIONS

US 7,186,244 B1, 03/2007, Hunt et al. (withdrawn)
(Continued)

*Primary Examiner* — Philip R Wiest
*Assistant Examiner* — Alessandro R Del Priore
(74) *Attorney, Agent, or Firm* — Knobbe, Martens, Olson & Bear, LLP

(57) ABSTRACT

Disclosed herein are several embodiments of a negative pressure apparatus and methods of using the same in the treatment of wounds. Some embodiments are directed towards improved fluidic connectors configured to transmit irrigation fluid and to apply aspiration to a wound, for example using softer, kink-free conformable layers. Some embodiments may comprise a first channel for delivering irrigation fluid to the wound and a second channel for transmitting negative pressure and removing fluid comprising irrigation fluid and wound exudate from the wound, wherein the channels comprise a flexible spacer material. Some embodiments are directed toward an irrigation manifold attachable to or incorporated as part of a distal end of an irrigation and aspiration fluidic connector.

21 Claims, 14 Drawing Sheets

Related U.S. Application Data

(60) Provisional application No. 61/822,254, filed on May 10, 2013.

(51) Int. Cl.
*A61M 39/10* (2006.01)
*A61M 3/02* (2006.01)

(52) U.S. Cl.
CPC ............ *A61M 1/90* (2021.05); *A61M 3/0279* (2013.01); *A61M 39/105* (2013.01)

(58) Field of Classification Search
CPC ............... A61M 39/00; A61M 1/84–98; A61F 13/00068; A61P 17/02
See application file for complete search history.

(56) References Cited

U.S. PATENT DOCUMENTS

| | | |
|---|---|---|
| 3,367,332 A | 2/1968 | Groves |
| 3,568,675 A | 3/1971 | Harvey |
| 3,624,821 A | 11/1971 | Henderson |
| 3,786,801 A | 1/1974 | Sartorius |
| 3,922,957 A | 12/1975 | Ogle et al. |
| 3,943,734 A | 3/1976 | Fleissner |
| 4,136,696 A | 1/1979 | Nehring |
| 4,178,938 A | 12/1979 | Au |
| 4,180,074 A | 12/1979 | Murry et al. |
| 4,224,945 A | 9/1980 | Cohen |
| 4,382,441 A | 5/1983 | Svedman |
| 4,466,431 A | 8/1984 | Tharrat et al. |
| 4,529,402 A | 7/1985 | Weilbacher et al. |
| 4,530,360 A | 7/1985 | Duarte |
| 4,587,101 A | 5/1986 | Marsoner et al. |
| 4,605,399 A | 8/1986 | Weston et al. |
| 4,650,462 A | 3/1987 | DeSatnick et al. |
| 4,657,006 A | 4/1987 | Rawlings et al. |
| 4,664,662 A | 5/1987 | Webster |
| 4,710,165 A | 12/1987 | McNeil et al. |
| 4,778,446 A | 10/1988 | Jensen |
| 4,787,888 A | 11/1988 | Fox |
| 4,813,931 A | 3/1989 | Hauze |
| 4,817,594 A | 4/1989 | Juhasz |
| 4,836,192 A | 6/1989 | Abbate |
| 4,872,450 A | 10/1989 | Austad |
| 4,921,492 A | 5/1990 | Schultz |
| 4,930,997 A | 6/1990 | Bennett |
| 4,969,880 A | 11/1990 | Zamierowski |
| 4,979,944 A | 12/1990 | Luzsicza |
| 5,009,635 A | 4/1991 | Scarberry |
| 5,010,883 A | 4/1991 | Rawlings et al. |
| 5,030,202 A | 7/1991 | Harris |
| 5,055,195 A | 10/1991 | Trasch et al. |
| 5,055,198 A | 10/1991 | Shettigar |
| 5,056,510 A | 10/1991 | Gilman |
| 5,100,396 A | 3/1992 | Zamierowski |
| 5,112,323 A | 5/1992 | Winkler et al. |
| 5,180,375 A | 1/1993 | Feibus |
| 5,261,893 A | 11/1993 | Zamierowski |
| 5,328,614 A | 7/1994 | Matsumura |
| 5,358,492 A | 10/1994 | Feibus |
| 5,360,398 A | 11/1994 | Grieshaber et al. |
| 5,419,768 A | 5/1995 | Kayser |
| 5,419,772 A | 5/1995 | Teitz et al. |
| 5,460,490 A | 10/1995 | Carr et al. |
| 5,487,889 A | 1/1996 | Eckert et al. |
| 5,490,984 A | 2/1996 | Freed |
| 5,498,338 A | 3/1996 | Kruger et al. |
| 5,527,293 A | 6/1996 | Zamierowski |
| 5,599,289 A | 2/1997 | Castellana |
| 5,636,643 A | 6/1997 | Argenta et al. |
| 5,645,081 A | 7/1997 | Argenta et al. |
| 5,662,924 A | 9/1997 | Rhodes |
| 5,676,650 A | 10/1997 | Grieshaber et al. |
| 5,678,564 A | 10/1997 | Lawrence et al. |
| 5,701,917 A | 12/1997 | Khouri |
| 5,733,253 A | 3/1998 | Headley et al. |
| 5,759,570 A | 6/1998 | Arnold |
| 5,778,890 A | 7/1998 | Lofgren et al. |
| 5,795,584 A | 8/1998 | Totakura et al. |
| 5,810,765 A | 9/1998 | Oda |
| 5,830,176 A | 11/1998 | Mackool |
| 5,885,237 A | 3/1999 | Kadash et al. |
| 5,893,862 A | 4/1999 | Pratt et al. |
| 5,904,659 A | 5/1999 | Duarte |
| 5,910,125 A | 6/1999 | Cummings et al. |
| 5,911,222 A | 6/1999 | Lawrence et al. |
| 5,941,859 A | 8/1999 | Lerman |
| 5,954,680 A | 9/1999 | Augustine |
| 5,976,117 A | 11/1999 | Dunshee et al. |
| 6,071,267 A | 6/2000 | Zamierowski |
| 6,142,982 A | 11/2000 | Hunt et al. |
| 6,156,334 A | 12/2000 | Meyer-Ingold et al. |
| 6,168,800 B1 | 1/2001 | Dobos et al. |
| 6,201,164 B1 | 3/2001 | Wulff et al. |
| 6,254,567 B1 | 7/2001 | Treu et al. |
| 6,345,623 B1 | 2/2002 | Heaton et al. |
| 6,398,767 B1 | 6/2002 | Fleischmann |
| 6,458,109 B1 | 10/2002 | Henley et al. |
| 6,465,708 B1 | 10/2002 | Augustine |
| 6,496,727 B1 | 12/2002 | Bernhard et al. |
| 6,520,982 B1 | 2/2003 | Boynton et al. |
| 6,527,745 B1 | 3/2003 | Kanda et al. |
| 6,626,891 B2 | 9/2003 | Ohmstede |
| 6,648,862 B2 | 11/2003 | Watson |
| 6,673,982 B1 | 1/2004 | Chen et al. |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,787,682 B2 | 9/2004 | Gilman |
| 6,800,074 B2 | 10/2004 | Henley et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,977,323 B1 | 12/2005 | Swenson |
| 6,979,324 B2 | 12/2005 | Bybordi et al. |
| D515,701 S | 2/2006 | Horhota et al. |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,087,807 B2 | 8/2006 | Stapf |
| 7,108,683 B2 | 9/2006 | Zamierowski |
| 7,195,624 B2 | 3/2007 | Lockwood |
| 7,198,046 B1 | 4/2007 | Argenta et al. |
| 7,211,060 B1 | 5/2007 | Talish et al. |
| 7,216,651 B2 | 5/2007 | Argenta et al. |
| 7,279,612 B1 | 10/2007 | Heaton et al. |
| 7,316,672 B1 | 1/2008 | Hunt et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,438,705 B2 | 10/2008 | Karpowicz et al. |
| 7,485,112 B2 | 2/2009 | Karpowicz et al. |
| 7,494,482 B2 | 2/2009 | Orgill et al. |
| 7,503,910 B2 | 3/2009 | Adahan |
| 7,507,870 B2 | 3/2009 | Nielsen et al. |
| 7,524,315 B2 | 4/2009 | Blott et al. |
| 7,531,711 B2 | 5/2009 | Sigurjonsson et al. |
| 7,532,953 B2 | 5/2009 | Vogel |
| 7,534,927 B2 | 5/2009 | Lockwood |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,625,362 B2 | 12/2009 | Boehringer et al. |

(56) References Cited

U.S. PATENT DOCUMENTS

| | | |
|---|---|---|
| 7,628,764 B2 | 12/2009 | Duarte et al. |
| 7,645,253 B2 | 1/2010 | Gura et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,678,090 B2 | 3/2010 | Risk, Jr. |
| 7,678,102 B1 | 3/2010 | Heaton |
| 7,686,785 B2 | 3/2010 | Boehringer et al. |
| 7,699,830 B2 | 4/2010 | Martin |
| 7,699,831 B2 | 4/2010 | Bengtson et al. |
| 7,722,582 B2 | 5/2010 | Lina et al. |
| 7,753,894 B2 | 7/2010 | Blott et al. |
| 7,794,438 B2 | 9/2010 | Henley et al. |
| 7,794,450 B2 | 9/2010 | Blott et al. |
| 7,862,718 B2 | 1/2011 | Doyen et al. |
| 7,867,206 B2 | 1/2011 | Lockwood et al. |
| 7,880,050 B2 | 2/2011 | Robinson et al. |
| 7,883,494 B2 | 2/2011 | Martin |
| 7,896,856 B2 | 3/2011 | Petrosenko et al. |
| 7,896,864 B2 | 3/2011 | Lockwood et al. |
| 7,910,791 B2 | 3/2011 | Coffey |
| 7,922,703 B2 | 4/2011 | Riesinger |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,988,680 B2 | 8/2011 | Lockwood et al. |
| 8,021,347 B2 | 9/2011 | Vitaris et al. |
| 8,062,272 B2 | 11/2011 | Weston |
| 8,062,331 B2 | 11/2011 | Zamierowski |
| 8,070,773 B2 | 12/2011 | Zamierowski |
| 8,075,503 B2 | 12/2011 | Jaeb |
| 8,080,702 B2 | 12/2011 | Blott et al. |
| 8,083,712 B2 | 12/2011 | Biggie et al. |
| 8,100,887 B2 | 1/2012 | Weston et al. |
| 8,105,295 B2 | 1/2012 | Blott et al. |
| 8,114,126 B2 | 2/2012 | Heaton et al. |
| 8,123,781 B2 | 2/2012 | Zamierowski |
| 8,128,615 B2 | 3/2012 | Blott et al. |
| 8,133,211 B2 | 3/2012 | Cavanaugh, II et al. |
| 8,147,468 B2 | 4/2012 | Barta et al. |
| 8,148,595 B2 | 4/2012 | Robinson et al. |
| 8,152,785 B2 | 4/2012 | Vitaris |
| 8,158,844 B2 | 4/2012 | McNeil |
| 8,162,907 B2 | 4/2012 | Heagle |
| 8,162,909 B2 | 4/2012 | Blott et al. |
| 8,168,848 B2 | 5/2012 | Lockwood et al. |
| 8,188,331 B2 | 5/2012 | Barta et al. |
| 8,192,409 B2 | 6/2012 | Hardman et al. |
| 8,202,261 B2 | 6/2012 | Kazala, Jr. et al. |
| 8,235,955 B2 | 8/2012 | Blott et al. |
| 8,241,261 B2 | 8/2012 | Randolph et al. |
| 8,246,592 B2 | 8/2012 | Lockwood et al. |
| 8,251,979 B2 | 8/2012 | Malhi |
| 8,257,327 B2 | 9/2012 | Blott et al. |
| 8,298,200 B2 | 10/2012 | Vess et al. |
| 8,348,910 B2 | 1/2013 | Blott et al. |
| 8,357,188 B2 | 1/2013 | Boynton et al. |
| 8,361,043 B2 | 1/2013 | Hu et al. |
| 8,372,049 B2 | 2/2013 | Jaeb et al. |
| 8,376,972 B2 | 2/2013 | Fleischmann |
| 8,377,017 B2 | 2/2013 | Wilkes |
| 8,382,731 B2 | 2/2013 | Johannison |
| 8,398,614 B2 | 3/2013 | Blott et al. |
| D679,819 S | 4/2013 | Peron |
| D679,820 S | 4/2013 | Peron |
| 8,529,548 B2 | 9/2013 | Blott et al. |
| 8,529,578 B2 | 9/2013 | Daniels et al. |
| 8,535,296 B2 | 9/2013 | Blott et al. |
| 8,647,327 B2 | 2/2014 | Larsson et al. |
| 8,734,410 B2 | 5/2014 | Hall et al. |
| 8,747,887 B2 | 6/2014 | Coffey |
| 8,758,313 B2 | 6/2014 | Blott et al. |
| 8,771,244 B2 | 7/2014 | Eckstein et al. |
| 8,791,316 B2 | 7/2014 | Greener |
| 8,801,685 B2 | 8/2014 | Armstrong et al. |
| 8,814,842 B2 | 8/2014 | Coulthard et al. |
| D714,433 S | 9/2014 | Armstrong et al. |
| 8,834,451 B2 | 9/2014 | Blott et al. |
| 8,843,327 B2 | 9/2014 | Vernon-Harcourt et al. |
| 8,845,619 B2 | 9/2014 | Blott et al. |
| 8,882,746 B2 | 11/2014 | Blott et al. |
| 8,905,985 B2 | 12/2014 | Allen et al. |
| 8,915,896 B2 | 12/2014 | Sanders et al. |
| 8,926,592 B2 | 1/2015 | Blott et al. |
| 8,998,866 B2 | 4/2015 | Hicks |
| 9,017,302 B2 | 4/2015 | Vitaris et al. |
| 9,044,569 B2 | 6/2015 | Blott et al. |
| 9,044,579 B2 | 6/2015 | Blott et al. |
| 9,050,398 B2 | 6/2015 | Armstrong et al. |
| 9,061,095 B2 | 6/2015 | Adie et al. |
| 9,107,998 B2 | 8/2015 | Pratt et al. |
| D746,435 S | 12/2015 | Armstrong et al. |
| 9,205,001 B2 | 12/2015 | Blott et al. |
| RE45,864 E | 1/2016 | Peron |
| 9,226,737 B2 | 1/2016 | Dunn |
| 9,227,000 B2 | 1/2016 | Fink et al. |
| 9,289,542 B2 | 3/2016 | Blott et al. |
| D755,980 S | 5/2016 | Jakobsen et al. |
| 9,327,065 B2 | 5/2016 | Albert et al. |
| 9,452,245 B2 | 9/2016 | Jaeb et al. |
| 9,474,654 B2 | 10/2016 | Heagle et al. |
| RE46,289 E | 1/2017 | Peron |
| 9,539,373 B2 | 1/2017 | Jones et al. |
| 9,642,750 B2 | 5/2017 | Albert et al. |
| 9,681,993 B2 | 6/2017 | Wu et al. |
| D804,014 S | 11/2017 | Armstrong et al. |
| 9,877,872 B2 | 1/2018 | Mumby et al. |
| 9,907,703 B2 | 3/2018 | Allen et al. |
| 9,956,389 B2 | 5/2018 | Armstrong et al. |
| 9,974,695 B2 | 5/2018 | Albert et al. |
| 9,999,547 B2 | 6/2018 | Albert et al. |
| 10,406,037 B2 | 9/2019 | Albert et al. |
| RE48,117 E | 7/2020 | Albert et al. |
| 11,058,588 B2 | 7/2021 | Albert et al. |
| 2001/0020145 A1 | 9/2001 | Satterfield et al. |
| 2001/0029956 A1 | 10/2001 | Argenta |
| 2001/0043943 A1 | 11/2001 | Coffey |
| 2002/0016570 A1 | 2/2002 | Cartledge |
| 2002/0068913 A1 | 6/2002 | Fleischmann |
| 2002/0082567 A1 | 6/2002 | Lockwood et al. |
| 2002/0114847 A1 | 8/2002 | Peshoff |
| 2002/0138036 A1 | 9/2002 | Babaev |
| 2002/0198504 A1 | 12/2002 | Risk et al. |
| 2003/0021775 A1 | 1/2003 | Freeman |
| 2003/0093041 A1 | 5/2003 | Risk, Jr. et al. |
| 2003/0109855 A1 | 6/2003 | Solem et al. |
| 2003/0134332 A1 | 7/2003 | Boykin, Jr. |
| 2003/0144619 A1 | 7/2003 | Augustine |
| 2003/0148959 A1 | 8/2003 | Quirk et al. |
| 2003/0171675 A1 | 9/2003 | Rosenberg |
| 2003/0175798 A1 | 9/2003 | Raees et al. |
| 2003/0211137 A1 | 11/2003 | Sierra |
| 2003/0212431 A1 | 11/2003 | Brady et al. |
| 2004/0001878 A1 | 1/2004 | DeBusk et al. |
| 2004/0019252 A1 | 1/2004 | Hirata |
| 2004/0077977 A1 | 4/2004 | Ella et al. |
| 2004/0127845 A1 | 7/2004 | Renz et al. |
| 2004/0241214 A1 | 12/2004 | Kirkwood et al. |
| 2005/0090787 A1 | 4/2005 | Risk et al. |
| 2005/0101940 A1 | 5/2005 | Radl et al. |
| 2005/0107756 A1 | 5/2005 | McCraw |
| 2005/0130299 A1 | 6/2005 | Suzuki |
| 2005/0137539 A1 | 6/2005 | Biggie et al. |
| 2006/0029675 A1 | 2/2006 | Ginther |
| 2006/0100586 A1 | 5/2006 | Karpowicz |
| 2006/0172000 A1 | 8/2006 | Cullen et al. |
| 2006/0229586 A1* | 10/2006 | Faries, Jr. ............ A61M 27/00 604/506 |
| 2007/0032763 A1 | 2/2007 | Vogel |
| 2007/0292397 A1 | 12/2007 | McNulty et al. |
| 2008/0033325 A1 | 2/2008 | Van Der Hulst |
| 2008/0033330 A1 | 2/2008 | Moore |
| 2008/0091133 A1 | 4/2008 | Matter |
| 2008/0125697 A1 | 5/2008 | Gao |

(56) References Cited

U.S. PATENT DOCUMENTS

| | | |
|---|---|---|
| 2008/0195017 A1 | 8/2008 | Robinson et al. |
| 2008/0208147 A1 | 8/2008 | Argenta et al. |
| 2008/0226720 A1 | 9/2008 | Kemp et al. |
| 2009/0012483 A1* | 1/2009 | Blott ............... A61M 27/00 604/315 |
| 2009/0012501 A1 | 1/2009 | Boehringer et al. |
| 2009/0054855 A1 | 2/2009 | Blott et al. |
| 2009/0124988 A1 | 5/2009 | Coulthard |
| 2009/0131892 A1 | 5/2009 | Karpowicz et al. |
| 2009/0157016 A1 | 6/2009 | Adahan |
| 2009/0163882 A1 | 6/2009 | Koch et al. |
| 2009/0221977 A1 | 9/2009 | Blott et al. |
| 2009/0227968 A1 | 9/2009 | Vess |
| 2009/0264837 A1 | 10/2009 | Adahan |
| 2009/0293887 A1 | 12/2009 | Wilkes et al. |
| 2009/0299249 A1 | 12/2009 | Wilkes et al. |
| 2009/0299255 A1 | 12/2009 | Kazala, Jr. et al. |
| 2009/0299257 A1 | 12/2009 | Long et al. |
| 2009/0299303 A1 | 12/2009 | Seegert |
| 2009/0299308 A1 | 12/2009 | Kazala et al. |
| 2009/0299340 A1 | 12/2009 | Kazala et al. |
| 2009/0312723 A1 | 12/2009 | Blott et al. |
| 2010/0016767 A1* | 1/2010 | Jones ............... A61M 25/00 601/10 |
| 2010/0069850 A1 | 3/2010 | Fabo |
| 2010/0069885 A1* | 3/2010 | Stevenson ............... A61M 1/90 604/540 |
| 2010/0094234 A1 | 4/2010 | Ramella et al. |
| 2010/0122417 A1 | 5/2010 | Vrzalik et al. |
| 2010/0137775 A1 | 6/2010 | Hu et al. |
| 2010/0160901 A1 | 6/2010 | Hu et al. |
| 2010/0249733 A9 | 9/2010 | Blott et al. |
| 2010/0312202 A1* | 12/2010 | Henley ............... A61M 35/30 604/319 |
| 2010/0324510 A1 | 12/2010 | Andresen et al. |
| 2011/0004172 A1 | 1/2011 | Eckstein et al. |
| 2011/0028917 A1 | 2/2011 | Hall |
| 2011/0130712 A1 | 6/2011 | Topaz |
| 2011/0172615 A2 | 7/2011 | Greener |
| 2011/0184361 A1 | 7/2011 | Crojzat et al. |
| 2011/0213319 A1* | 9/2011 | Blott ............... A61M 27/00 604/291 |
| 2011/0257572 A1 | 10/2011 | Locke et al. |
| 2011/0257593 A1 | 10/2011 | Kalpin et al. |
| 2011/0313373 A1 | 12/2011 | Riesinger |
| 2011/0313374 A1 | 12/2011 | Lockwood et al. |
| 2012/0040013 A1 | 2/2012 | Owens et al. |
| 2012/0302976 A1 | 11/2012 | Locke et al. |
| 2013/0138036 A1* | 5/2013 | Solomon ............... A61M 3/0283 604/43 |
| 2013/0144240 A1 | 6/2013 | Ellis |
| 2013/0165821 A1 | 6/2013 | Freedman et al. |
| 2013/0172835 A1 | 7/2013 | Braga et al. |
| 2013/0296818 A1 | 11/2013 | Bradford et al. |
| 2013/0310781 A1 | 11/2013 | Phillips et al. |
| 2013/0310809 A1 | 11/2013 | Armstrong |
| 2014/0135741 A1* | 5/2014 | Hamman ............... A61M 1/84 604/541 |
| 2014/0249493 A1 | 9/2014 | Hartwell |
| 2014/0343520 A1 | 11/2014 | Bennett et al. |
| 2015/0018786 A1 | 1/2015 | Locke et al. |
| 2015/0080788 A1 | 3/2015 | Blott et al. |
| 2015/0159066 A1 | 6/2015 | Hartwell et al. |
| 2015/0165182 A1 | 6/2015 | Pratt et al. |
| 2015/0190286 A1 | 7/2015 | Allen et al. |
| 2015/0231314 A1 | 8/2015 | Robinson et al. |
| 2015/0265754 A1 | 9/2015 | Blott et al. |
| 2016/0144084 A1 | 5/2016 | Collinson et al. |
| 2016/0354535 A1 | 12/2016 | Blott et al. |
| 2018/0304065 A1 | 10/2018 | Armstrong et al. |
| 2020/0100945 A1 | 4/2020 | Albert et al. |

FOREIGN PATENT DOCUMENTS

| | | |
|---|---|---|
| DE | 3 935 818 | 5/1991 |
| DE | 4 012 232 | 10/1991 |
| DE | 4 102 684 | 8/1992 |
| DE | 197 22 075 | 10/1998 |
| DE | 198 44 355 | 4/2000 |
| EP | 0 298 726 | 1/1989 |
| EP | 0 174 803 | 8/1991 |
| EP | 0 325 771 | 9/1993 |
| EP | 0 392 640 | 6/1995 |
| EP | 0 441 418 | 7/1995 |
| EP | 0 465 601 | 1/1997 |
| EP | 0 751 757 | 1/1997 |
| EP | 0 853 950 | 7/1998 |
| EP | 0 777 504 | 10/1998 |
| EP | 1 018 967 | 7/2000 |
| EP | 0 865 304 | 7/2001 |
| EP | 1 169 071 | 1/2002 |
| EP | 1 897 569 | 8/2002 |
| EP | 0 708 620 | 5/2003 |
| EP | 1 088 569 | 8/2003 |
| EP | 0 993 317 | 9/2003 |
| EP | 1 565 219 | 12/2003 |
| EP | 1 440 667 | 7/2004 |
| EP | 1 448 261 | 8/2004 |
| EP | 1 100 574 | 2/2005 |
| EP | 1 513 478 | 3/2005 |
| EP | 0 688 189 | 6/2005 |
| EP | 1 284 777 | 4/2006 |
| EP | 0 982 015 | 8/2006 |
| EP | 0 620 720 | 11/2006 |
| EP | 2 145 636 | 5/2007 |
| EP | 2 145 637 | 5/2007 |
| EP | 1 227 853 | 1/2008 |
| EP | 1 476 217 | 3/2008 |
| EP | 1 233 808 | 7/2008 |
| EP | 1 977 776 | 10/2008 |
| EP | 1 807 184 | 12/2008 |
| EP | 2 127 690 | 12/2009 |
| EP | 1 905 465 | 1/2010 |
| EP | 2 172 164 | 4/2010 |
| EP | 2 319 550 | 5/2011 |
| EP | 1 578 477 | 9/2011 |
| EP | 2 366 721 | 9/2011 |
| EP | 1 487 389 | 10/2011 |
| EP | 2 529 766 | 12/2012 |
| EP | 2 545 946 | 3/2013 |
| EP | 2 623 138 | 8/2013 |
| EP | 2 650 028 | 10/2013 |
| EP | 2 659 915 | 11/2013 |
| EP | 2 650 027 | 1/2014 |
| EP | 2 628 500 | 5/2014 |
| EP | 1 339 366 | 6/2014 |
| EP | 2 051 675 | 6/2014 |
| EP | 1 545 644 | 8/2014 |
| EP | 2 801 388 | 11/2014 |
| EP | 1 742 683 | 2/2016 |
| FR | 1 163 907 | 10/1958 |
| GB | 1549756 | 8/1979 |
| GB | 2307180 | 5/1997 |
| GB | 2336546 | 10/1999 |
| GB | 2344531 | 7/2000 |
| GB | 2378392 | 2/2003 |
| JP | S62-279885 | 12/1987 |
| JP | 2001-314479 | 11/2001 |
| JP | 2001-525688 | 12/2001 |
| JP | 2003-154003 | 5/2003 |
| JP | 2004-121819 | 4/2004 |
| WO | WO 1984/01904 | 5/1984 |
| WO | WO 1987/00759 | 2/1987 |
| WO | WO 1999/01173 | 1/1999 |
| WO | WO 2000/007653 | 2/2000 |
| WO | WO 2000/064394 | 11/2000 |
| WO | WO 2002/043634 | 6/2002 |
| WO | WO 2002/092783 | 11/2002 |
| WO | WO 2003/057070 | 7/2003 |
| WO | WO 2003/073970 | 9/2003 |
| WO | WO 2003/086232 | 10/2003 |

(56) References Cited

FOREIGN PATENT DOCUMENTS

| | | |
|---|---|---|
| WO | WO 2003/101508 | 12/2003 |
| WO | WO 2004/018020 | 3/2004 |
| WO | WO 2004/024300 | 3/2004 |
| WO | WO 2004/037334 | 5/2004 |
| WO | WO 2005/016179 | 2/2005 |
| WO | WO 2005/061025 | 7/2005 |
| WO | WO 2005/070480 | 8/2005 |
| WO | WO 2005/082435 | 9/2005 |
| WO | WO 2005/102415 | 11/2005 |
| WO | WO 2005/105174 | 11/2005 |
| WO | WO 2005/105175 | 11/2005 |
| WO | WO 2005/105176 | 11/2005 |
| WO | WO 2006/014917 | 2/2006 |
| WO | WO 2007/006306 | 1/2007 |
| WO | WO 2007/016590 | 2/2007 |
| WO | WO 2007/019038 | 2/2007 |
| WO | WO 2007/041642 | 4/2007 |
| WO | WO 2007/085396 | 8/2007 |
| WO | WO 2007/092397 | 8/2007 |
| WO | WO 2007/095180 | 8/2007 |
| WO | WO 2007/106590 | 9/2007 |
| WO | WO 2007/106591 | 9/2007 |
| WO | WO 2007/120138 | 10/2007 |
| WO | WO 2007/123451 | 11/2007 |
| WO | WO 2008/008032 | 1/2008 |
| WO | WO 2008/012278 | 1/2008 |
| WO | WO 2008/027449 | 3/2008 |
| WO | WO 2008/042481 | 4/2008 |
| WO | WO 2008/043067 | 4/2008 |
| WO | WO 2008/100437 | 8/2008 |
| WO | WO 2008/100440 | 8/2008 |
| WO | WO 2008/100446 | 8/2008 |
| WO | WO 2008/131895 | 11/2008 |
| WO | WO 2008/135997 | 11/2008 |
| WO | WO 2008/140439 | 11/2008 |
| WO | WO 2008/141470 | 11/2008 |
| WO | WO 2009/002260 | 12/2008 |
| WO | WO 2009/146441 | 3/2009 |
| WO | WO 2009/068665 | 6/2009 |
| WO | WO 2009/086580 | 7/2009 |
| WO | WO 2009/088925 | 7/2009 |
| WO | WO 2009/111655 | 9/2009 |
| WO | WO 2009/137194 | 11/2009 |
| WO | WO 2009/140376 | 11/2009 |
| WO | WO 2009/145894 | 12/2009 |
| WO | WO 2009/158129 | 12/2009 |
| WO | WO 2010/006182 | 1/2010 |
| WO | WO 2010/014177 | 2/2010 |
| WO | WO 2010/033271 | 3/2010 |
| WO | WO 2010/033272 | 3/2010 |
| WO | WO 2010/033769 | 3/2010 |
| WO | WO 2010/051073 | 5/2010 |
| WO | WO 2010/059712 | 5/2010 |
| WO | WO 2010/059730 | 5/2010 |
| WO | WO 2010/078166 | 7/2010 |
| WO | WO 2010/120470 | 10/2010 |
| WO | WO 2010/147533 | 12/2010 |
| WO | WO 2011/049562 | 4/2011 |
| WO | PCT/US2011/041521 * 6/2011 ............ A61M 1/00 |
| WO | WO 2011/087871 | 7/2011 |
| WO | WO 2011/100851 | 8/2011 |
| WO | WO 2011/115908 | 9/2011 |
| WO | WO 2012/087376 | 6/2012 |
| WO | WO 2012/142002 | 10/2012 |
| WO | WO 2012/170744 | 12/2012 |
| WO | WO 2012/174672 | 12/2012 |
| WO | WO 2013/013938 | 1/2013 |
| WO | WO 2013/016239 | 1/2013 |
| WO | WO 2013/019438 | 2/2013 |
| WO | WO 2013/043972 | 3/2013 |
| WO | WO 2013/123005 | 8/2013 |
| WO | WO 2014/066057 | 5/2014 |
| WO | WO 2014/043238 | 9/2014 |
| WO | WO 2014/158526 | 10/2014 |
| WO | WO-2015022334 A1 | 2/2015 |
| WO | WO-2015022340 A1 | 2/2015 |
| WO | WO-2015026326 A1 | 2/2015 |

OTHER PUBLICATIONS

Bevan, D. et al., "Diverse and potent activities of HGF/SF in skin wound repair", Journal of Pathology, vol. 203, 2004, pp. 831-838, in 8 pages.

Columbia Electronic Encyclopedia, The: the effect of body temperature on wound healing, printed Jan. 16, 2009, in 3 pages. URL: http://encyclopedia2.thefreedictionary.com/body+temperature.

INSTECH Model P720 Peristaltic Pump Operation Manual, Dec. 1997, pp. 1-11, in 7 pages.

International Search Report and Written Opinion, re PCT Application No. PCT/IB2014/001682, dated Jan. 20, 2015.

International Preliminary Reporton Patentability, re PCT Application No. PCT/IB2014/001682, dated Nov. 19, 2015.

Kuznetsov, V.A. et al., "Vacuum and Vacuum-Sorption Treatment of Open Septic Wounds", in Second All-Union Conference "Wounds and Wound Infections" (Presentation Abstracts) (Moscow, USSR 1986) pp. 91-92, with English translation, in 5 pages.

Mitchell, R. et al., "Role of Stem Cells in Tissue Homeostasis", Pocket Companion to Robbins and Cotran Pathologic Basis of Disease, 7th Edition, 2006.

Teder, H. et al., "Continuous Wound Irrigation in the Pig," Journal of Investigative Surgery, vol. 3, 1990, pp. 399-407, in 9 pages.

The Wayback Machine, "Comfort advantages with AirX™," retrieved from http://web.archive.org/web/20090121000205/http://www.airx.eu:80/content/view/2/3/lang,en/, on Jan. 21, 2009, 1 page.

The Wayback Machine, "Moisture-Transporting Material," retrieved from http://web.archive.org/web/20090121001036/http://www.airx.eu/content/view/1/14/lang,en/, on Jan. 21, 2009, 1 page.

* cited by examiner

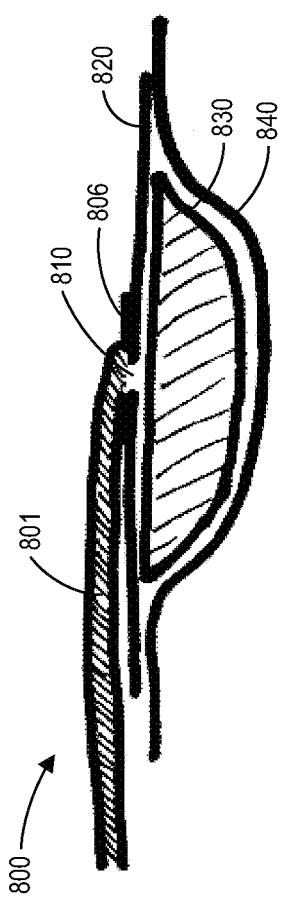
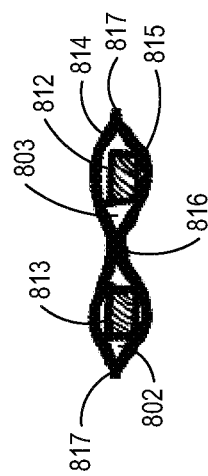
Figure 8A
Figure 8B

FLUIDIC CONNECTOR FOR IRRIGATION AND ASPIRATION OF WOUNDS

CROSS-REFERENCE TO RELATED APPLICATION

This application is a divisional application of U.S. application Ser. No. 14/889,825, filed on Nov. 6, 2015, which is a national stage application of International Patent Application No. PCT/IB2014/001682, filed on May 6, 2014, which claims the benefit of U.S. Provisional Application Ser. No. 61/822,254, filed May 10, 2013, the entirety of which is hereby incorporated by reference.

BACKGROUND

Field of the Invention

Embodiments described herein relate to apparatuses, systems, and methods the treatment of wounds, for example by applying irrigation and aspiration to a wound via a fluidic connector.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines bacteria. However, further improvements in NPWT are needed to fully realize the benefits of treatment.

In previously filed U.S. Pat. Nos. 7,524,315 and 8,105,295, the entireties of each of which are hereby incorporated by reference, apparatuses, wound dressings, and methods for aspirating, irrigating and cleansing wounds are described. In some of the embodiments described therein, a wound is treated by the application of topical negative pressure (TNP) therapy for aspirating the wound, together with the further provision of additional fluid for irrigating and/or cleansing the wound, which fluid, comprising both wound exudates and irrigation fluid, is then drawn off by the aspiration. The aspiration and irrigation are typically provided via conduits passing through the dressing into the wound cavity.

Whilst such treatment methods work well in practice, the stiffness of the aspiration and irrigation conduits in such close proximity to the wound site can adversely affect the healing process. Patient movement or pressure onto the wound dressing may bring the healing wound into contact with the relatively inflexible conduits. Such force can cause disturbance of a wound bed which can damage a wound site. This can potentially cause delays in healing of the wound site. These conduits can also cause discomfort to the patient. The ability to create a fluid tight seal about the area where the conduits pass through the wound dressing can also be challenging.

It will also be appreciated that aspiration and irrigation conduits are prone to obstruction. The conduits may become obstructed by movement of the patient, which may cause part of the tube to bend and form a kink or may place pressure onto the tubing, substantially or fully blocking the flow of fluid through the tubing. This can reduce or eliminate the negative pressure and/or irrigation fluid being transmitted to the wound site. In embodiments employing a separate canister for fluid collection, obstruction of the aspirant conduit can also result in accumulation of excess wound exudate at the wound site.

SUMMARY OF THE INVENTION

Certain embodiments disclosed herein relate to improved fluidic connectors for providing aspiration and irrigation and having enhanced flexibility. Such fluidic connectors may have advantages over prior art dressings which may be more rigid and therefore uncomfortable for a patient, particularly when inserted into or located around sensitive wound areas. Other advantages may be that the fluidic connectors described herein are less prone to obstruction than the more rigid conduits of the prior art. Also disclosed are improved methods of use and systems for use of the same, preferably in conjunction with negative pressure wound therapy.

In one embodiment, a fluidic connector for providing aspiration and irrigation to a wound site, comprises:
  a proximal end and a distal end and an elongate length extending therebetween;
  a top layer, a bottom layer and an intermediate layer each constructed from a flexible, liquid impermeable material and adhered to one another, wherein each of the layers has a proximal end and a distal end and elongate portions extending therebetween;
  an upper fluid passage between the top layer and the intermediate layer;
  a lower fluid passage between the intermediate layer and the bottom layer;
  one or more openings at or near a distal end of the upper fluid passage; and
  one or more openings at or near a distal end of the lower fluid passage;
  wherein each of the upper and lower fluid passages comprises a flexible, elongate spacer material between corresponding layers; and
  wherein one of the upper and lower fluid passages is configured to provide aspiration to the wound site, and the other of the upper and lower fluid passages is configured to provide irrigation fluid to the wound site.

In further embodiments, the spacer material of each of the upper and lower fluid passages may comprise at least one of a 3D knitted or 3D fabric material, foam, a porous material and non-woven material. The upper fluid passage configured to provide aspiration to the wound and the lower fluid passage may also be configured to provide irrigation fluid to the wound. The one or more openings at or near a distal end of the upper fluid passage may comprise an upwardly facing opening in the top layer. The one or more openings at or near a distal end of the upper fluid passage may comprise a distally facing opening between the top and intermediate layers. The spacer material of the upper fluid passage may extend distally beyond the distally facing opening between the top and intermediate layers. The one or more openings at or near a distal end of the lower fluid passage may comprise a plurality of microporous openings in the bottom layer. Some embodiments can further comprise a fluid distributing layer positioned below the one or more openings at or near a distal end of the lower fluid passage. A distal end of the spacer material of the lower fluid passage may extend distally beyond a distal end of the spacer material of the upper fluid passage.

In further embodiments, the fluid passage configured to provide irrigation fluid to the wound site may comprise a plurality of radially extending arms at a distal end thereof. Some embodiments may comprise plurality of openings along each of the radially extending arms. The radially extending arms may comprise spacer material therein. The radially extending arms may be formed in part by the bottom layer. The radially extending arms may be part of a manifold attached to the bottom layer with the radially extending arms in fluid communication with the one or more openings at or near the distal end of the lower fluid passage.

Some embodiments may further comprise adhesive along at least a portion of the bottom layer for adhering the bottom layer to skin adjacent a wound. The corresponding layers of each of the upper and lower fluid passages may have side portions along sides of the elongate spacer material that are parallel to and adhered to each other. The fluidic connector is sufficiently soft to conform to a patient's skin along a substantial portion of a length of the fluidic connector.

In another embodiment, a method of treating a wound of a patient, comprises:
  positioning the fluidic connector of any one of the preceding claims into a wound with the one or more openings of the upper and lower fluid passages positioned within the wound and the proximal end of the fluidic connector positioned outside of the wound with a portion of the fluidic connector positioned against the skin of the patient;
  covering the wound with a wound cover, wherein the wound cover is sealed to skin surrounding the wound and seals against the portion of the fluidic connector positioned against the skin of the patient;
  providing negative pressure to the wound through one of the upper and lower fluid passages; and
  providing irrigation fluid to the wound through the other of the upper and lower fluid passages.

Further embodiments may further comprise positioning a porous wound filler into contact with the wound, and positioning the distal end of the fluidic connector over the porous wound filler. Some embodiments may further comprise positioning a porous wound filler over the distal end of the fluidic connector, and positioning the wound cover over the porous wound filler that is positioned over the distal end of the fluidic connector.

In another embodiment, a system for treatment of a wound comprises:
  a sealing membrane for covering the wound;
  a dressing adapted to be positioned in the wound; and
  a fluidic connector capable of being operably associated, in use, with the wound cavity, the fluidic connector comprising:
    a proximal end and a distal end and an elongate length extending therebetween;
    a first layer of flexible film,
    a second layer of flexible film sealed around a perimeter to the first layer of flexible film, thereby defining an aspirant channel, wherein at least one aspiration opening in the distal end of the first layer of flexible film is configured to transmit aspiration to the wound cavity, and
    a third layer of flexible film sealed around a perimeter to the second layer of flexible film, thereby defining an irrigation channel, wherein at least one irrigation opening in the distal end of the third layer is configured to transmit irrigation fluid to the wound.

In further embodiments, each of the aspirant channel and irrigation channel may comprise a flexible, elongate spacer material between corresponding layers. The spacer material may extend through the at least one aspiration opening.

In further embodiments, an aspirant conduit may be provided at the proximal end of the aspirant channel. A vacuum means may be configured to apply negative pressure to the wound through the aspirant conduit and the aspirant channel. A waste collection canister may be configured to connect to a proximal end of the aspirant conduit. An irrigation conduit may be provided at the proximal end of the irrigation channel. An irrigation source may be configured to provide irrigation fluid to the wound through the irrigation conduit and the irrigation channel.

Further embodiments may comprise a manifold attached over the at least one irrigation orifice, the manifold having a lower surface, the manifold adapted to deliver irrigation fluid across a larger area than the distal end of the irrigation opening. The manifold may comprise a plurality of radially extending arms. Each of the plurality of radially extending arms may comprise a plurality of irrigation orifices in the lower surface. The wound filler may comprise first and second layers of a wound filling material, and wherein the distal end of the fluidic connector is positioned between the first and second layers of wound filling material.

In another embodiment, a fluidic connector for providing aspiration and irrigation to a wound site, may comprise:
  a top layer and a bottom layer each constructed from a flexible, liquid impermeable material, wherein each of the layers has a proximal end and a distal end and elongate portions extending therebetween, and wherein each of the layers has a left edge and a right edge and a center portion therebetween;
  a left seal extending along the length of the left edges of the top and bottom layers, a right seal extending along the length of the right edges of the top and bottom layers, and a middle seal extending along at least a portion of the length of the center portions of the top and bottom layers;
  a left fluid passage between the top and bottom layers, further defined by the left seal and the middle seal;
  a right fluid passage between the top and bottom layers, further defined by the middle seal and the right seal;
  one or more openings in the bottom layer at or near a distal end of the left and right fluid passages; and
  at least one applicator portion attached to or integral with the bottom layer at a distal end of the bottom layer;
  wherein each of the left and right fluid passages comprises a flexible, elongate spacer material between the top and bottom layers; and
  wherein one of the left and right fluid passages is configured to provide aspiration to the wound site, and the other of the left and right fluid passages is configured to provide irrigation fluid to the wound site.

In another embodiment, a fluidic connector for providing aspiration and irrigation to a wound site, may comprise:
  a proximal end and a distal end and an elongate length extending therebetween;
  a first fluid passage and a second fluid passage positioned side-by-side and joined together along at least a portion of the elongate length, each of the fluid passages containing an elongate spacer material; and
  at least one applicator portion at the distal end;

wherein the first fluid passage is configured to provide aspiration to a wound site, and the second fluid passage is configured to provide irrigation fluid to the wound site.

In further embodiments, the first fluid passage and the second fluid passage may be separated at the distal end, each fluid passage being connected to a separate applicator portion. The first fluid passage and the second fluid passage may be formed between flexible layers of liquid impermeable material.

In another embodiment, a method of treating a wound of a patient, may comprise:

positioning a wound cover over a wound, wherein the wound cover seals to skin surrounding the wound;

positioning a fluidic connector as described above over an opening in the wound cover;

providing negative pressure to the wound through one of the fluid passages; and providing irrigation fluid to the wound through the other of the fluid passages.

In another embodiment, a system for treatment of a wound, may comprise:

a sealing membrane for covering the wound;

a wound filler adapted to be positioned in the wound; and a fluidic connector as described above configured to be sealed over an opening in the sealing membrane.

Further embodiments may comprise a source of negative pressure configured to be in fluid communication with one of the fluid passages, and a source of irrigation fluid configured to be in fluid communication with the other of the fluid passages.

BRIEF DESCRIPTION OF THE DRAWINGS

FIGS. 8A-D illustrate various views of an embodiment of a fluidic connector for irrigation and aspiration of wounds having side-by-side channels.

DETAILED DESCRIPTION

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. Wounds include, but are not limited to, open wounds, incisions, lacerations, abrasions, contusions, burns, diabetic ulcers, pressure ulcers, stoma, surgical wounds, trauma and venous ulcers or the like. Treatment of such wounds can be performed using negative pressure wound therapy, wherein a reduced or negative pressure can be applied to the wound to facilitate and promote healing of the wound. It will also be appreciated that the negative pressure systems and methods as disclosed herein may be applied to other parts of the body, and are not necessarily limited to treatment of wounds.

Figure 1A:
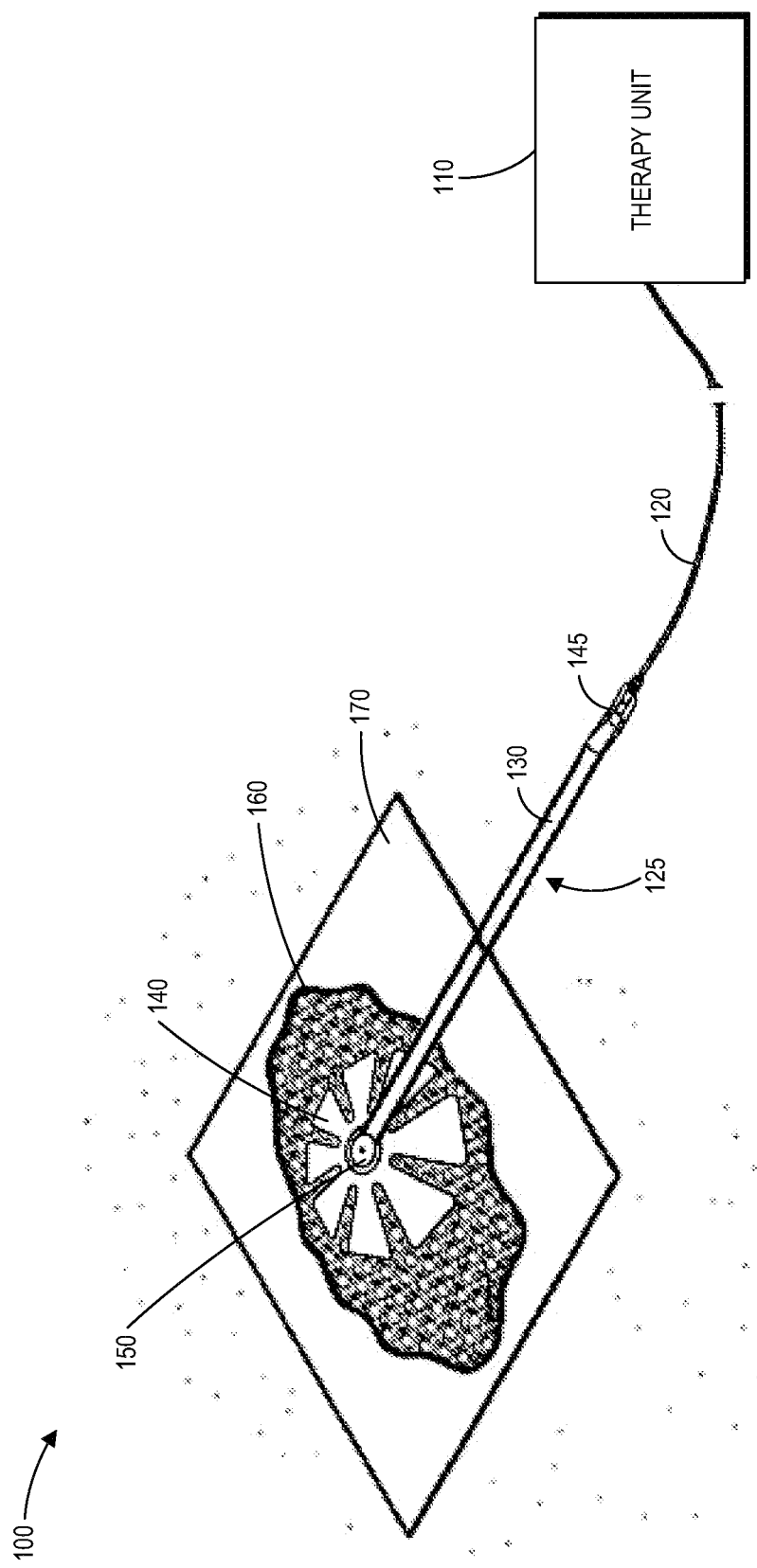
FIG. 1A illustrates an embodiment of a negative pressure wound treatment system capable of aspirating and irrigating a wound.
Figure 1B:
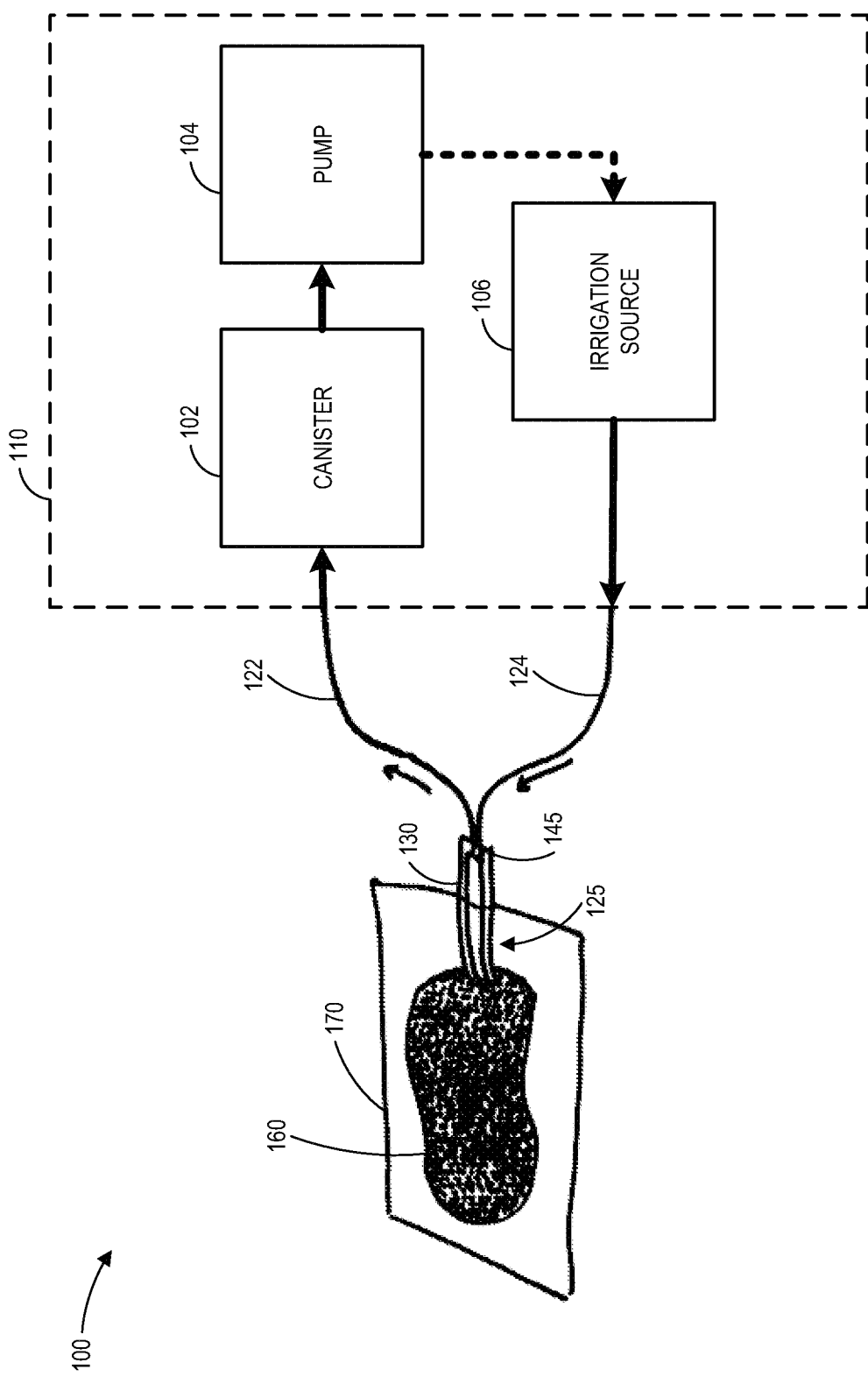
FIG. 1B illustrates an embodiment of a negative pressure wound treatment system capable of aspirating and irrigating a wound.

With reference initially to FIGS. 1A-B, treatment of a wound in certain embodiments of the application uses a system 100 comprising a therapy unit 110, a fluidic connector 125 having an elongate bridge portion 130 extending between a proximal end 145 and a distal end 150, a manifold 140 at the distal end 150, a wound filler 160 and a drape 170. A single conduit 120 (FIG. 1A) or multiple conduits 122, 124 (FIG. 1B) may be utilized to connect the fluidic connector 125 to the therapy unit 110.

The wound may be filled with a filling or packing material 160. Suitable materials for the wound filler 160 may be porous, pressure resistant materials which resists crushing at negative pressures of a maximum of about −250 mmHg below atmospheric, and materials which may also serve to maintain a uniform pressure distribution over the area of the wound. Such materials are known to those skilled in the art and may include Gazetex™ gauze bandage roll supplied by Derma Sciences Inc., CAVICARE™ supplied by Smith & Nephew, open cell reticulated polyurethane foam, polyvinyl alcohol foam, Mepitel™ supplied by Molnlycke, or compressed foam, for example. As described further below, multiple wound fillers may be used, for example a first wound filler that is placed in contact with the wound and a second wound filler that may be placed over the fluidic connector 125.

In some embodiments, as illustrated in FIG. 1A, the fluidic connector 125 may be configured to be placed in the wound, either above and/or under one or more wound fillers 160. As described in further detail below, the fluidic connector 125 is configured to provide deliver both aspiration and irrigation to the wound. As illustrated, a conduit 120 with at least two interior channels or lumens (one for aspiration, one for irrigation) may connect the proximal end of the elongate bridge 130 of the fluidic connector to an integrated therapy unit 110. The integrated therapy unit 110 may contain means for providing negative pressure, such as a vacuum pump, and means for supplying irrigation fluid. For example, an integrated unit could be an irrigation and aspiration unit such as Ulta™ supplied by KCI. In other embodiments, separate irrigation and aspiration units may be provided.

Over the wound filler 160 and fluidic connector 125 is the drape 170. The drape 170 may be a flexible film, for example polyurethane. With the elongate bridge 130 of the fluidic connector 125 positioned against the skin surrounding the wound, the drape 170 may be laid over the wound and sealed to the patient's healthy skin surrounding the wound, creating a substantially sealed wound cavity to which negative pressure may be transmitted. The drape 170 is therefore also laid over the elongate bridge 130 of the fluidic connector 125, forming a seal with an upper surface of the elongate bridge as well as the skin on both sides of the elongate bridge. In some embodiments, a lower surface of the fluidic connector 125 may also be sealed to the patient's skin. For example, adhesive may be applied under the fluidic connector 125 prior to placement of the connector over the patient's healthy skin, or may be provided along the elongate bridge 130 during manufacture and protected prior to use by a release layer. The drape 170 and/or fluidic connector 125 may be effectively sealed to the patient's healthy skin surrounding the wound by means of an adhesive on the wound-facing lower surface of the drape, for example a pressure-sensitive adhesive. However, the term "sealed" is not an absolute requirement nor practically attainable since many flexible drape membrane materials are composed of semi-permeable plastics materials which are well known to those skilled in the art. The term semi-permeable is defined as being permeable to water vapour and gases but not liquids or air, having a transmissibility of moisture vapour greater than approximately 500 g/sq·m/per 24 hr period. Furthermore, there is almost inevitably some leakage between the skin to which the sealing drape is adhered due to hairs and/or other skin surface irregularities and/or imperfections which are not easily completely sealed in absolute terms. Examples of the types of self-adhesive, flexible dressing drape materials which are ordinarily used in TNP type therapy as sealing membranes over and around wounds are listed hereinabove and are well known to those skilled in the art and will not be elaborated on further herein unless necessary.

Some embodiments may employ separate units for irrigation and aspiration, as illustrated in FIG. 1B. For example, an aspirant conduit 122 may enable fluid communication between the proximal end of the fluidic connector 125 and a pump 104 for generating aspiration at the wound site. Liquid comprising wound exudate and/or irrigation fluid may be carried away from the wound through the aspirant conduit 122. A waste canister 102 may optionally be disposed between the fluidic connector 130 and the pump 104 for collection of fluid, for example irrigation fluid and wound exudates, which has been removed from the wound site. In some embodiments, the canister 102 may be integrated into the pump 104. However, in other embodiments, the wound filler 160 may act as a waste canister to collect and store wound exudate removed from a wound site beneath the drape 170.

An irrigation conduit 124 may enable fluid communication between the proximal end of the fluidic connector 125 and an irrigation source 106. Irrigation fluid from the irrigation source may be drawn into the wound using the same pump 104 that provides aspiration through conduit 122, or a separate irrigation pump may also be used. Further arrangements for providing aspiration and irrigation to the wound, as well as other systems, apparatuses and methods that may be incorporated with the features described herein, are described in U.S. Pat. Nos. 7,524,315 and 8,105,295, the entireties of each of which are hereby incorporated by reference.

Figure 2:
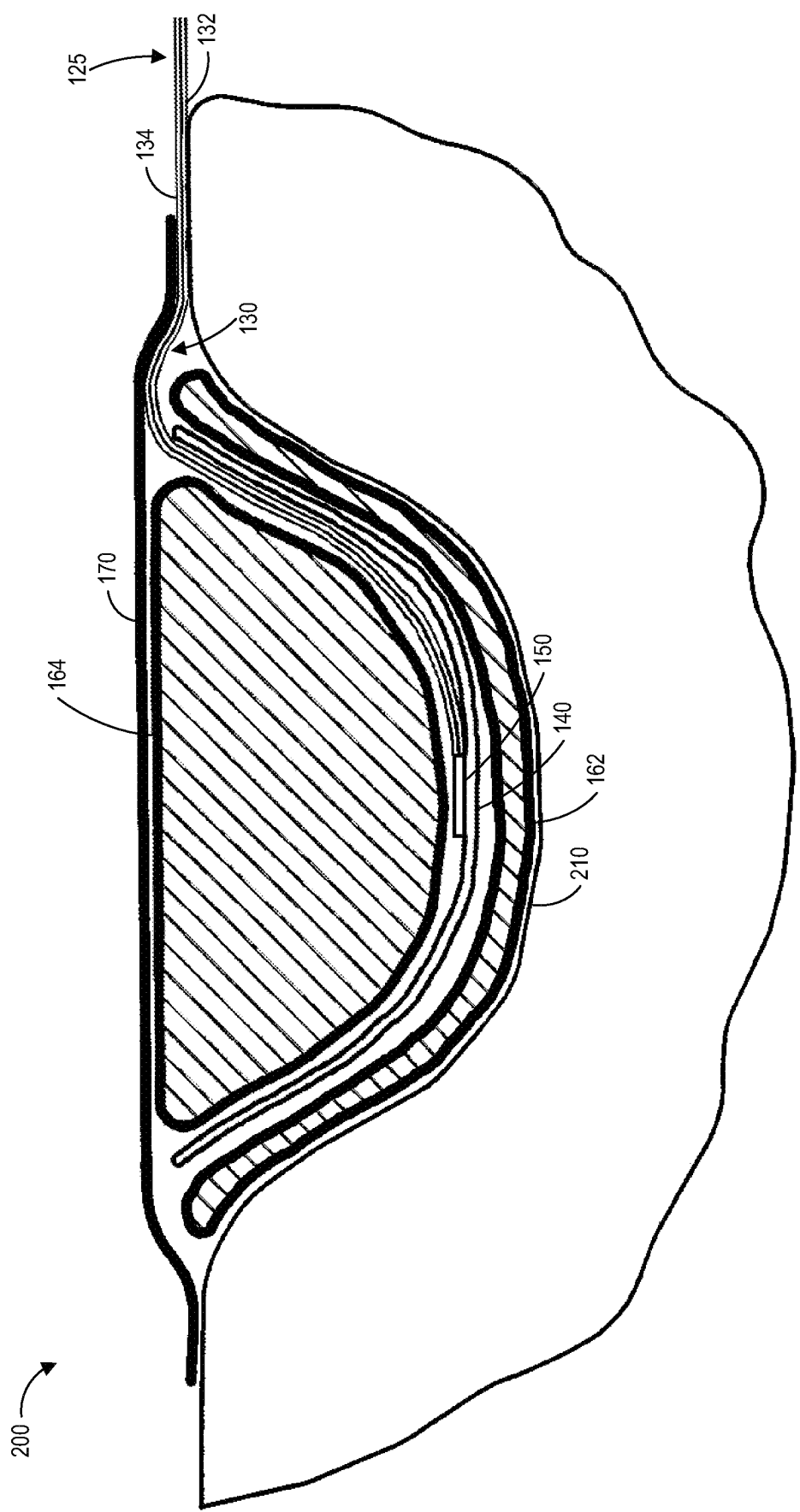
FIG. 2 illustrates a cross sectional view of an embodiment of a fluidic connector for irrigation and aspiration used with a negative pressure wound treatment system.

FIG. 2 illustrates a cross sectional view of a wound site 200 comprising a wound cavity 210 packed with a first wound filling layer 162, above which is located a fluidic connector 125 similar to what's shown in FIG. 1A. The fluidic connector comprises an irrigation manifold 140 located at a distal end 150 of an elongate bridge 130, wherein the elongate bridge 130 comprises an irrigation channel 132 and an aspiration channel 134. As illustrated and as further described below, in some embodiments the aspiration channel is an upper channel above a lower irrigation channel, though in other embodiments this arrangement can be reversed, or the channels could be side-by-side. A second wound filling layer 164 is positioned above the fluidic connector and the cavity 210 is sealed with a flexible drape 170. With the elongate bridge of the fluidic connector 125 positioned against the skin surrounding the wound, the drape 170 may be laid over the wound and the elongate bridge, and may be sealed to the upper surface and sides of the elongate bridge and the patient's healthy skin surrounding the wound, for example by means of a pressures sensitive adhesive provided on the lower (wound facing) surface of the drape. Sealing the drape to the bridge and the healthy skin may create a substantially sealed wound cavity to which negative pressure may be transmitted. In other embodiments, the drape may comprise an upper layer and a lower layer, and the fluidic connector may extend between the upper and lower layers.

Figure 3A:
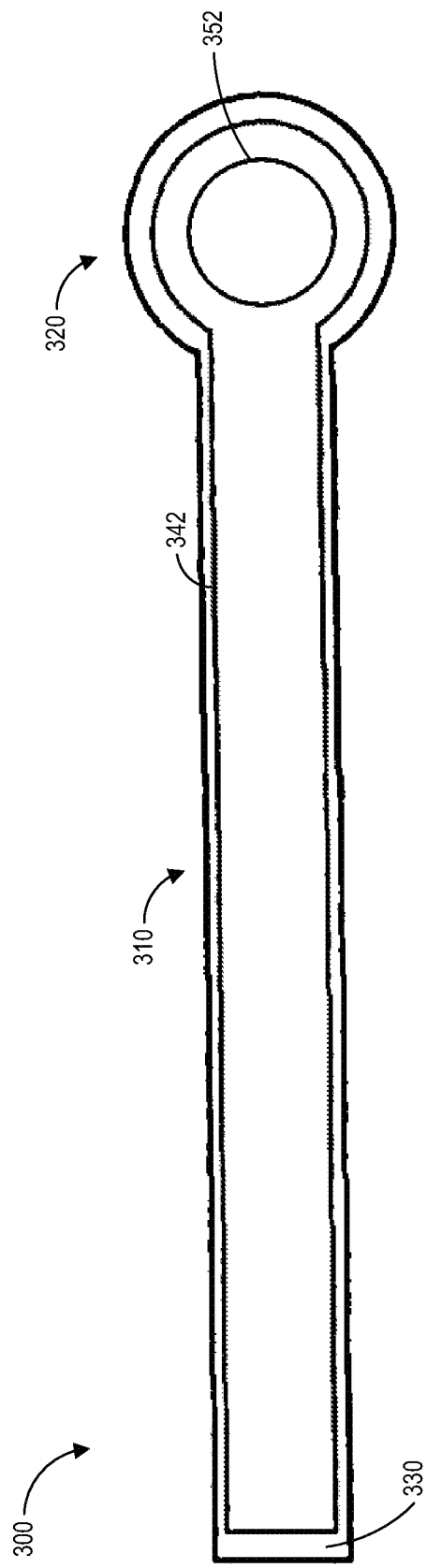
FIG. 3A illustrates a top view of an embodiment of a fluidic connector for irrigation and aspiration of wounds.
Figure 3B:
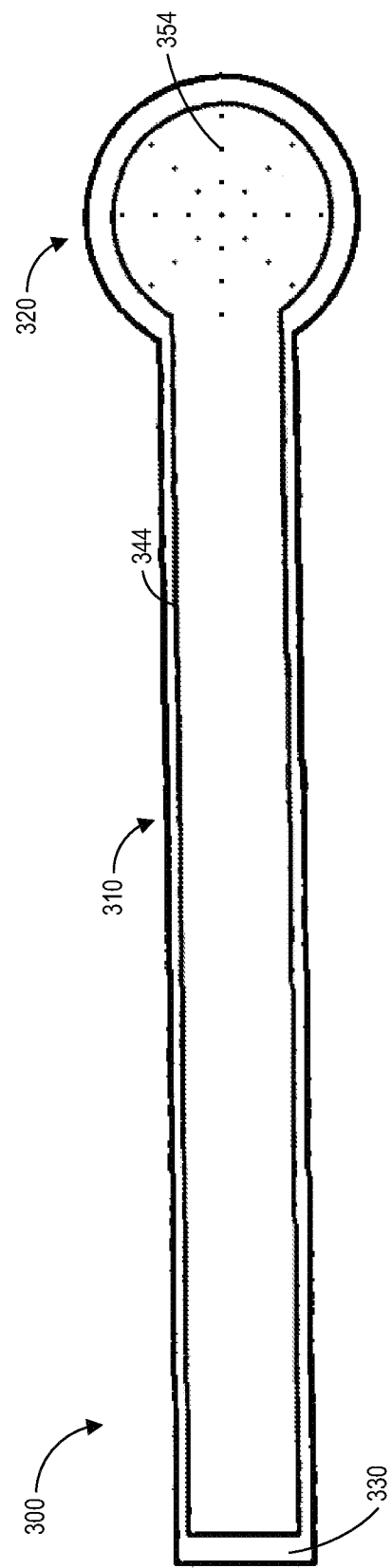
FIG. 3B illustrates a bottom view of an embodiment of a fluidic connector for irrigation and aspiration of wounds.
Figure 3C:
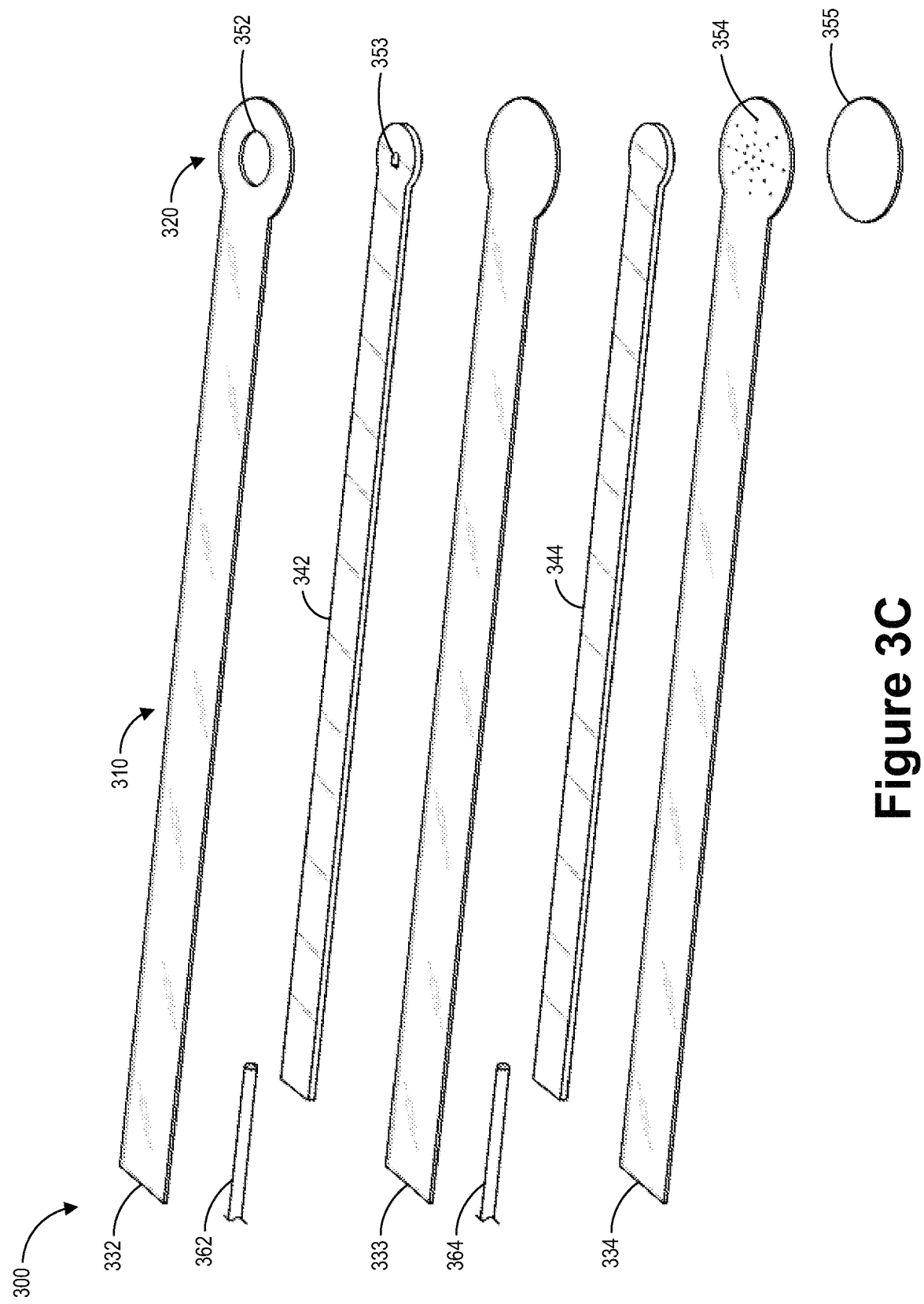
FIG. 3C illustrates an exploded view of the layers of an embodiment of a fluidic connector for irrigation and aspiration of wounds.

As illustrated the wound may be filled with two layers of packing material 162, 164, and the distal end 150 of the fluidic connector and the manifold 140 may be disposed between the two layers. The manifold 140 may be in fluid communication with the irrigation channel 132 at the distal end 150 of the elongate bridge 130, and as illustrated may be provided below the irrigation channel 132 to distribute irrigation fluid to the wound. However, in some embodiments such as shown in FIGS. 3A-3C described below, the distal end 150 of the fluidic connector may be adapted to provide irrigation fluid to the cavity 210, and the lower manifold may be optionally not included. The lower surface of the fluidic connector distal end 150 or manifold 140 may provide irrigation fluid through at least one orifice by means of irrigation channel 132, as described further below.

Using irrigation fluid that passes through the irrigation channel 132, the lower wound filler 162 in contact with the wound cavity surface 210 may be irrigated with fluid beneficial for the healing process. Negative pressure may be applied to the wound site through the aspiration channel 132 and distributed through the upper wound filler 164 which may substantially fill the wound. In some embodiments, the lower wound filling layer 162 may be a thin sheet shaped to line the wound surface, and the upper wound filling layer 164 may be shaped to maintain a substantially flat surface approximately level with the patient's healthy skin when the wound cavity is under negative pressure. In some embodiments, as described further below, the wound site may be aspirated through at least one orifice at the distal end of the fluidic connector 150.

The drape 170 may be placed over the bridge portion 130 and substantially seal to the top surface and sides of the bridge portion and the exposed healthy skin of the patient. The drape may seal, for example, by a pressure-sensitive adhesive provided on the lower surface of the drape. The substantially sealed drape 170 and wound cavity surface 210 define a wound cavity which may be provided with negative pressure.

FIGS. 3A-C illustrate an embodiment of a fluidic connector 300 which may be used in the systems of FIGS. 1A-B and for treatment of a wound cavity such as in FIG. 2. In these embodiments, the fluidic connector does not have a separate manifold such as manifold 140 described above. FIG. 3A illustrates a top view of the fluidic connector 300, FIG. 3B illustrates a bottom view of the fluidic connector 300, and FIG. 3C illustrates an exploded view of the fluidic connector 300.

The fluidic connector 300 may comprise an elongate bridge portion 310 and an enlarged rounded (e.g. circular) end 320. The distal end of the fluidic connector is depicted as having an enlarged circular shape, although it will be appreciated that any suitable shape may be used and that the distal end need not be enlarged. The fluidic connector 300 may comprise a sealed perimeter 330 defining one or more fluid transmission channels.

The fluidic connector 300 may comprise multiple layers of a flexible film material sealed to one another in a perimeter 330. As shown in FIG. 3C, a three layer structure may be provided, comprising a bottom layer 334, an intermediate layer 333, and a top layer 332 to form an upper fluid passage and a lower fluid passage. Each of these layers may be made of a flexible film, and in some embodiments may be transparent. Some embodiments of the flexible film may be formed from a soft polymer, for example a polyethylene, a polyvinyl chloride, a silicone or polyurethane having a hardness of 30 to 90 on the Shore A scale.

At the distal end of the fluidic connector, the top layer may have an opening 352 through which aspiration to the wound can be provided. Also at the distal end of the fluidic connector, the bottom layer may have one or more openings 354 for providing irrigation to the wound. In certain embodiments, the lower surface of the enlarged end 320 of the lower film layer 334 may be provided with an adhesive for attaching to a manifold, as described below, or simply for attaching the lower surface to skin surrounding the wound.

The top, intermediate, and bottom film layers 332, 333, 334 may be substantially the same shape as one another, and may each comprise an elongate bridge portion and an enlarged (e.g., rounded or circular) portion at a distal end thereof. Alternatively, the layers need not have the same shape, and in one embodiment, the intermediate and bottom layers may have a larger distal end than the top layer to provide a greater area to distribute irrigation to the wound.

The top layer 332 may be sealed to one or both of the intermediate layer 333 and the bottom later 334, for example by heat welding, radio frequency welding, laser welding, or ultrasonic welding. In some embodiments, the bottom layer 334 may be substantially flat and the top layer 332 and intermediate layer 333 may be slightly larger than the bottom layer 334 in order to accommodate the height of the spacer layers (described below) and seal to the bottom layer. Such an arrangement is also shown with respect to FIG. 6. In other embodiments, the top layer 332 and bottom layer 334 may be substantially the same size and may be slightly larger than the intermediate layer 333, and the layers may be sealed together approximately at the middle of the height of the fluidic connector 300 such that the intermediate layer 333 is substantially flat. Such an arrangement is also shown with respect to FIG. 7.

In some embodiments, the elongate bridge portions of the film layers may have a length of 10 cm (or about 10 cm) or more, more preferably a length of 20 cm (or about 20 cm) or more and in some embodiments, may be about 69 cm (or 27 cm) long. Some embodiments of the entire fluidic connector, from a proximal most edge of the top and bottom layers to a distalmost edge of the top and bottom layers, may be between 20 cm and 80 cm (or about 20 cm to about 80 cm) long, more preferably about 60 cm and 80 cm (or between about 60 cm and about 80 cm) long, for example about 70 cm long. In some embodiments, the elongate bridge portion of the flexible film layers may have a width of between 1 cm and 4 cm (or between about 1 cm and about 4 cm), and in one embodiment, is about 2.5 cm wide. The ratio of the length of the elongate bridge portion to the width may in some embodiments exceed 6:1, and may more preferably exceed 8:1 or even 10:1. The diameter of the circular portion may be about 3.5 cm in some embodiments, or may be much larger to better distribute aspiration and irrigation to the wound.

The fluidic connector may comprise a first spacer layer 342 and second spacer layer 344, the first spacer 342 layer positioned between the top layer 332 and the intermediate layer 333 and the second spacer layer 344 positioned between the intermediate layer 333 and the bottom layer 334. In some embodiments, the first spacer layer may be used as an aspirant layer and the lower spacer layer may be used to transmit irrigation fluid. The aspirant spacer layer 342 may optionally comprise a hole 353 located beneath the hole 352 in the top film layer 332 to facilitate transmission of negative pressure.

The spacer layers may be made of any suitable material, for example material resistant to collapsing in at least one direction, thereby enabling effective transmission of negative pressure or irrigation fluid therethrough. In particular, the spacer layers ensure that an open channel can be maintained to communicate negative pressure or irrigation fluid through the fluidic connector 300 to the wound area. The spacer layer 342 should remain open under the typical pressures that will be applied during negative pressure wound therapy. The spacer layers are preferably formed of a material having a three dimensional structure. For example, a knitted or woven spacer fabric (for example Baltex 7970 weft knitted polyester) or a non-woven fabric could be used. The spacer layers may also comprise materials such foams, including open-cell foams such as polyethylene or polyurethane foam, meshes, non-woven materials, and fluid channels.

In some embodiments, each of the spacer layers 342, 344 may comprise a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Some embodiments of the fluidic connector 300 may employ the same fabric for both the upper and lower spacer layers 342, 344. However, in other embodiments, a first material may be used as a spacer layer for the aspirant channel and a second material may be used as a spacer layer for the irrigation channel, the first and second materials having properties optimized for the purpose of aspiration or irrigation, respectively. Alternatively, some embodiments may utilize spacer fabric only for the aspirant channel so that the channel remains open even under negative pressure, and the irrigation channel may simply comprise a fluid passage encapsulated by the surrounding film layers.

Although the illustrated embodiment has been generally described as having an upper aspirant channel and a lower irrigation channel, it will be appreciated that many variations of this configuration are possible. For example, some embodiments may employ more than two fluid transmission channels. Other embodiments may only employ an irrigation channel. In some embodiments the fluid transmission channels may be side by side, or the irrigation channel may be above the aspirant channel.

In some embodiments, the elongated bridge of the spacer layers 342, 344 may have dimensions in the same ranges as the bridge portions of the film layers described above though slightly smaller, and in one embodiment is about 25.5 cm long and about 1.5 cm wide. Similarly, the diameter of the enlarged distal portion 320 of the spacer layers may be slightly smaller than the diameters of the enlarged ends of the film layers, and in one embodiment is about 2 cm. Some embodiments of a spacer layer may have adhesive on one or both of its proximal and distal ends (e.g., one or more dabs of adhesive) in order to secure the spacer layer to one or both of the adjacent film layers. Adhesive may also be provided along a portion or the entire length of one or both of the spacer layers. In other embodiments, one or both of the spacer layers may be freely movable within the sealed chamber of the adjacent film layers.

Some embodiments may optionally comprise a first conduit 362 and a second conduit 364 at the proximal end of the elongate bridge portion 310 of the fluidic connector 300. In some embodiments, the first conduit 362 may be in fluid communication with spacer layer 342, and may transmit fluid including irrigation fluid and wound exudates away from a wound site through orifice 352, as well as providing negative pressure to the wound site. The second conduit 364 may be in fluid communication with spacer layer 344, and may transmit irrigation fluid through a plurality of holes 354 located in the lower film layer 334. In some embodiments, an optional fluid distributing layer 355 can be positioned below the plurality of holes 354 in the lower film layer 334 to aid in even distribution of fluid across part of all of a wound site. For example, fluid distributing layer 355 can be a perforated film or microporous layer such as polyurethane foamed film or compressed foam. Fluid distributing layer 355 can be welded to, glued to, or laminated over the lower surface of the lower film layer 334 below the plurality of holes 354 in various embodiments. In some embodiments, fluid distributing layer 355 can be pre-attached to the lower surface of the lower film layer 334. In other embodiments, the fluid distributing layer 355 can be positioned between the lower surface of the lower film layer 334 and a wound to be treated. As described above, in other embodiments such as shown in FIG. 1A, a single conduit having multiple lumens may also be utilized to transmit negative pressure and deliver irrigation fluid to the fluidic connector 300.

Figure 3D:
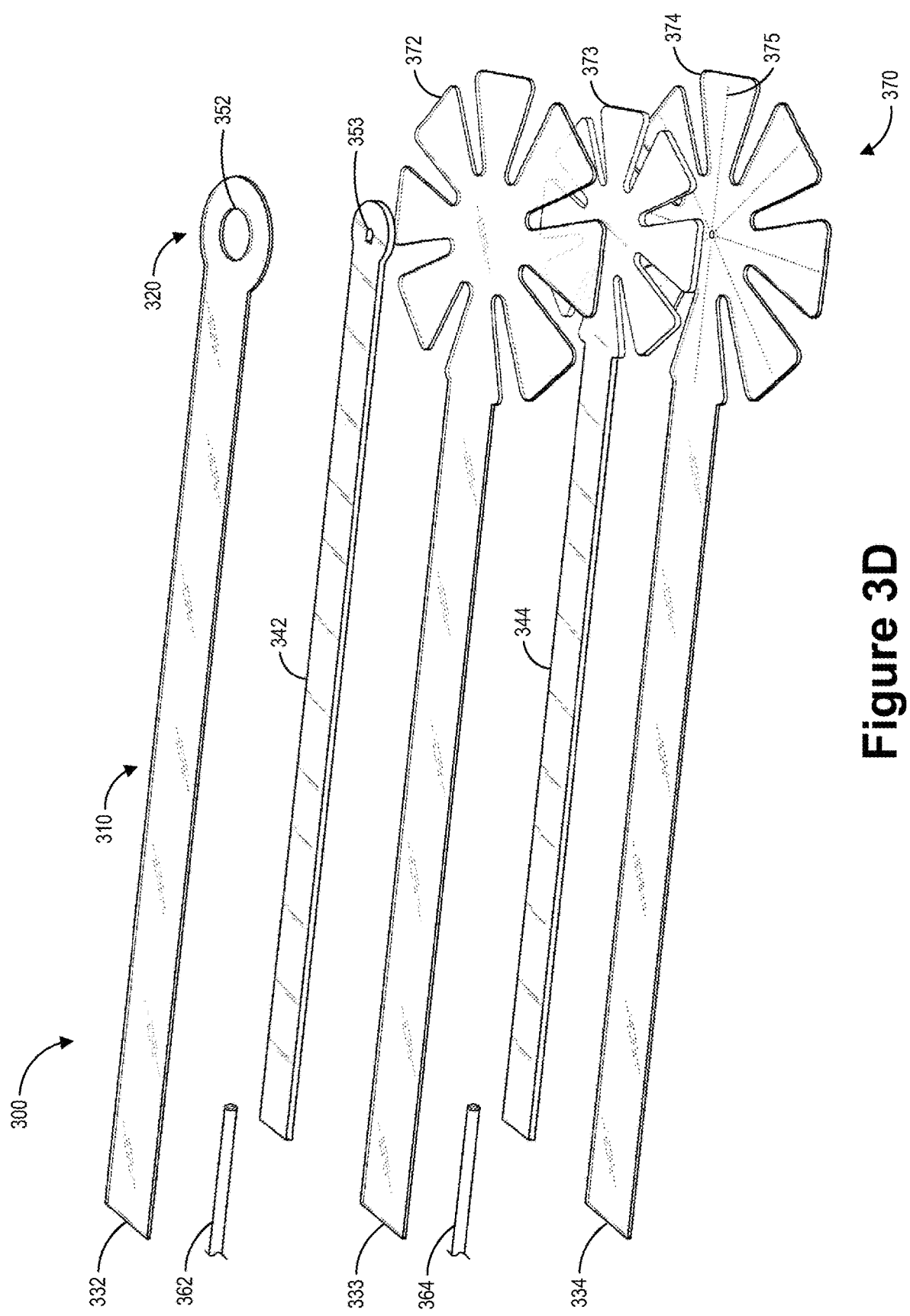
FIG. 3D illustrates an exploded view of the layers of an embodiment of a fluidic connector with an integrated manifold.

FIG. 3D illustrates an embodiment of a fluidic connector 300 in which the two layers of flexible film of the manifold 370 form part of the intermediate layer 333 and bottom layer 334. Thus, the intermediate layer 333 and bottom layer 334 are shaped such that a manifold 370 is simply a part of the fluidic connector. The manifold top layer 372 is formed by the distal end of the intermediate layer 333, the manifold spacer material 373 is formed by the distal end of the spacer layer 344, and the manifold bottom layer 374 is formed by the distal end of the bottom layer 334. A plurality of pores 375 may be provided in the lower manifold layer 374 for distribution of irrigation fluids. The pores 375 may cover substantially all of the surface of the manifold layer 374. In such embodiments, the spacer material 373 in the manifold may also be part of the spacer material 344 of FIG. 3C. The manifold portion 373 of the spacer layer 334 extends distally past the end of the upper spacer layer 342. In the illustrated embodiment, the manifold top layer 372, manifold spacer material 373, and manifold bottom layer 374 are integrally formed as extensions of the intermediate film layer 333, spacer layer 344, and lower film layer 334 of the elongate bridge portion 310, respectively. However, in other embodiments the manifold 370 may be a separate structure attachable to a lower surface of the bottom film layer 334 of the elongate bridge portion 310, for example by adhesive or welding.

Figure 3E:
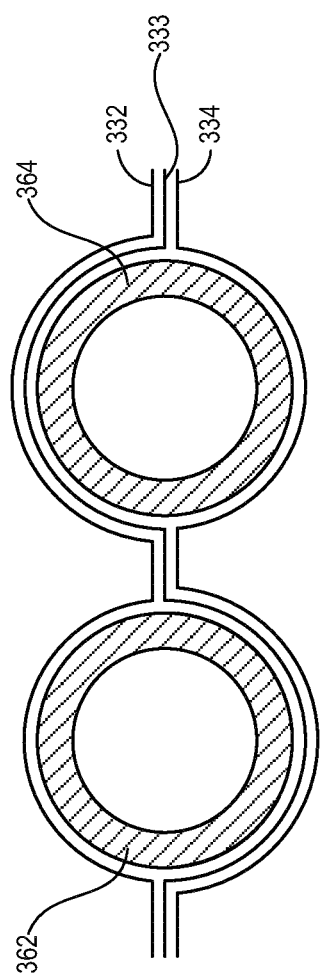
FIG. 3E illustrates a cross sectional view of one end of an embodiment of a fluidic connector for irrigation and aspiration of wounds.

FIG. 3E illustrates a cross sectional view of one example arrangement of the conduits and flexible film layers at the proximal end of the elongate bridge portion 310 of the fluidic connector 300. As illustrated, the intermediate film layer 333 is positioned underneath the first conduit 362 and above the second conduit 364, however this can be reversed in other embodiments. Accordingly, the first conduit 362 and the second conduit 364 are positioned in a side-by-side configuration. The lower film layer 334 is positioned underneath the intermediate film layer 333 under the first conduit 362 and underneath the second conduit 364. The upper film layer 332 is positioned above the first conduit 362 and above the intermediate film layer 333 above the second conduit 364. Such a side-by-side configuration of the conduits 362, 364 can reduce the height of the fluidic connector compared to an arrangement in which conduits 362, 364 are positioned above and below one another. Although the conduits 362, 364 are arranged in a side-by-side configuration, the upper spacer layer 342 and lower spacer layer 344 with which conduits 362, 364 (respectively) are in fluid communication can remain positioned above and below one another.

Figure 4B:
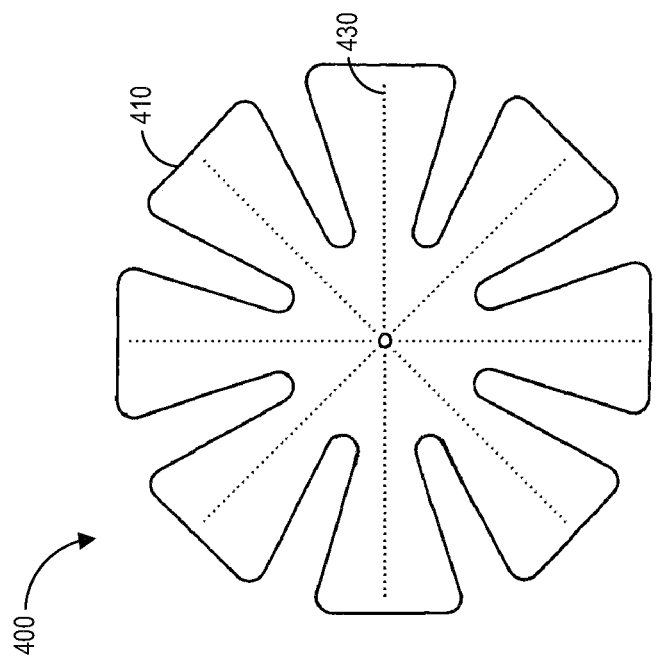
FIG. 4B illustrates a bottom view of an embodiment of a manifold for use with an irrigation fluidic connector.
Figure 4A:
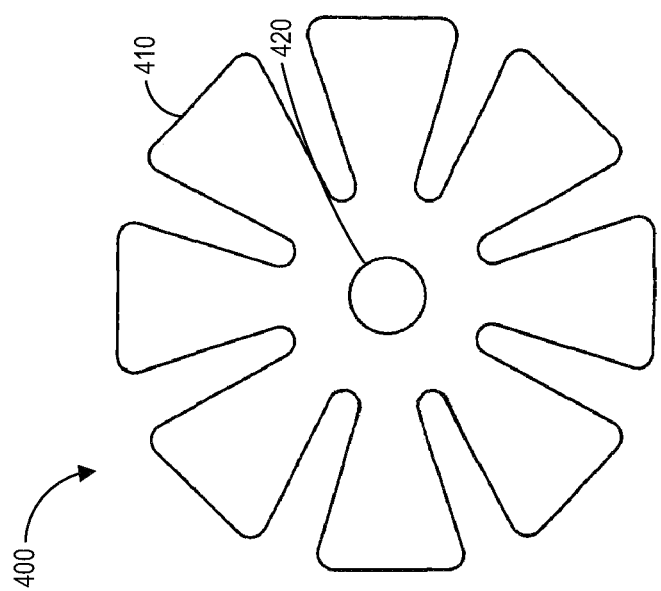
FIG. 4A illustrates a top view of an embodiment of a manifold for use with an irrigation fluidic connector.

FIGS. 4A-4B illustrate top and bottom views of an embodiment of a manifold 400 attachable to a fluidic connector, such as described in FIGS. 3A-C, or that may be incorporated as part of the fluidic connector. The manifold may advantageously distribute the irrigation fluid over a larger area than the enlarged end of the fluidic connector. The manifold may comprise a plurality of radially extending arms 410. In some embodiments, the arms 410 may be sized larger than a wound such that they may be made to fit the wound by folding the arms 410 back on themselves. Other embodiments of the manifold may employ a variety of other suitable shapes, including shapes with more or less radially extending arms, circular shapes, etc.

The manifold may comprise two layers of a flexible film such as used for the fluidic connector described above, wherein the layers are sealed around a perimeter. The encapsulated inner area of the manifold may contain a layer of spacer fabric or other spacer material. Suitable materials include those discussed above as well as reticulated filtration polyurethane foams with small apertures or pores. The top film layer of the manifold may be provided with a hole 420 for accepting irrigation fluid from the fluidic connector. The hole 420 may communicate with the plurality of holes 354 of the fluidic connector 300, or may communicate with a single larger hole at the enlarged end of the bottom layer of the fluidic connector 300.

As shown in FIG. 4B, some embodiments of the manifold may comprise an array of holes 430 provided through the lower layer of the manifold for outlet of irrigation fluid. Other embodiments may utilize different configurations of holes than the illustrated embodiment, or may employ a porous membrane as the lower surface. For example, in some embodiments the holes 430, or pores or micropores used instead of or in addition to the holes 430, may cover substantially all of the area of the radially extending arms 410. In some embodiments the holes 430, or pores or micropores used instead of or in addition to the holes 430, may be arranged in regions of the radially extending arms 410 or in patterns over a portion of the area of the radially extending arms 410.

The holes or pores of the manifold may be sized or otherwise configured in some embodiments so as to limit the maximum pressure at which irrigation fluid may be delivered to a wound. The pores may also be sized such that, at the desired flow rate, the fluid passes out of the manifold uniformly across its entire area, ensuring that the wound is uniformly irrigated. For example, some embodiments may limit the pressure of the fluid to approximately eight to twelve pounds per square inch. This may be advantageous as fluids delivered at high pressures may disturb the healing wound bed, and if the pressure exceeds approximately 15 psi, bacteria may be pushed further into a patient's wound. In other embodiments the irrigation fluid supply flow regulation may be accomplished by other means, such as a pump and/or feed pressure.

Figure 5A:
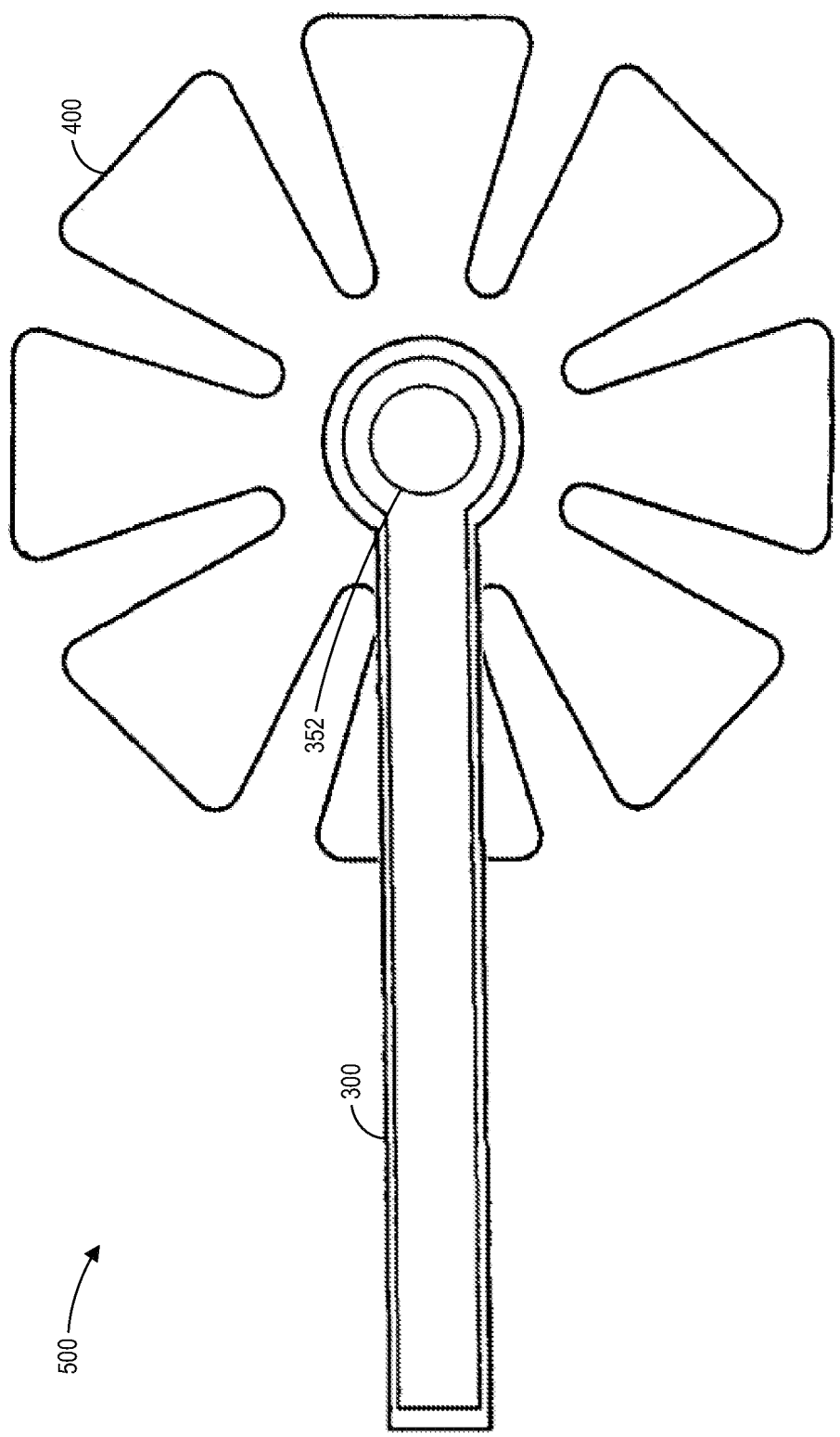
FIG. 5A illustrates a top view of an embodiment of a manifold attached to a fluidic connector for irrigation and aspiration of wounds.
Figure 5B:
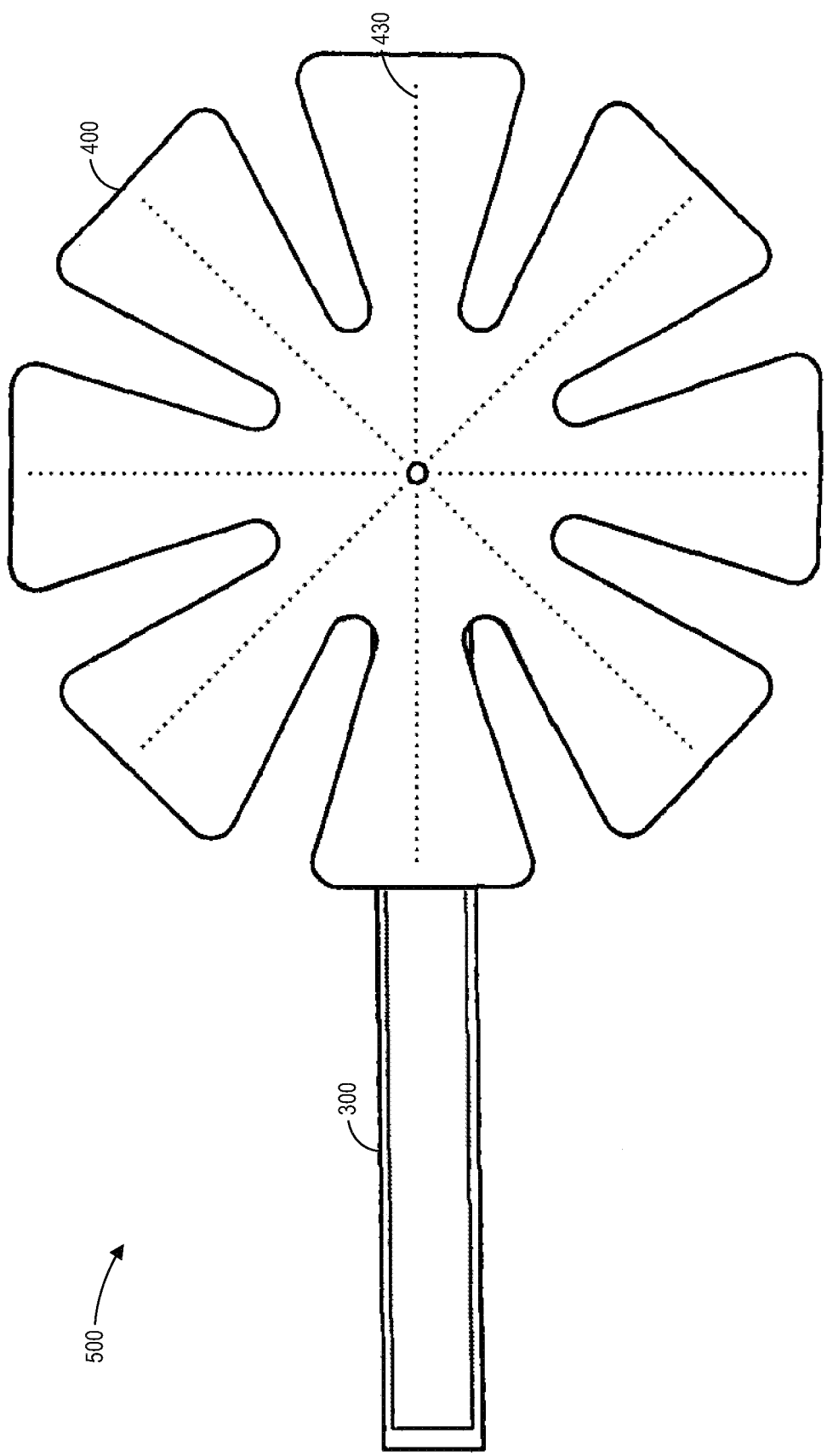
FIG. 5B illustrates a bottom view of an embodiment of a manifold attached to a fluidic connector for irrigation and aspiration of wounds.

FIG. 5A illustrates a top view of an embodiment of the fluidic connector 300 of FIGS. 3A-C attached to the manifold 400 of FIGS. 4A-B. The upper layer of the fluidic connector 300 has an orifice 352 for providing aspiration through the upper channel of the fluidic connector and for drawing fluid away from a wound. FIG. 5B illustrates a bottom view the fluidic connector 300 attached to the manifold 400. The lower layer of the manifold is provided with a plurality of orifices 430 for transmitting irrigation fluid to the wound. Some embodiments may employ very fine pore size foams for the lower layer, for example materials felted by heat and compression to produce a dense, porous film. The manifold may be attached to the fluidic connector during manufacture of the fluidic connector, such that the manifold is simply part of the fluidic connector. Alternatively, the manifold may be provided to a user separately from the fluidic connector and may be attached to the fluidic connector by the user. This may be advantageous to allow the user to select different manifolds depending on the needs of the patient.

Figure 5C:
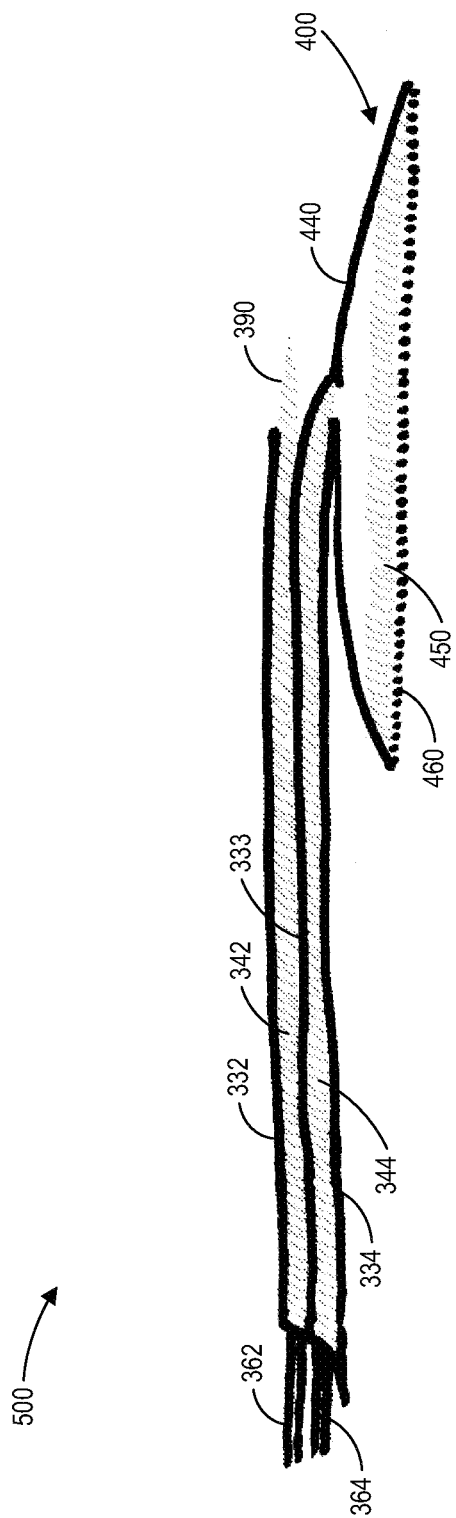
FIG. 5C illustrates a cross sectional side view of a manifold attached to a fluidic connector for irrigation and aspiration of wounds.

FIG. 5C illustrates a cross sectional side view of another embodiment of the fluidic connector 300 having a manifold 400. The upper film layer 440 and lower perforated film layer 460 of the manifold 400 are illustrated, encapsulating spacer layer 450. In the embodiment illustrated, a portion 390 of the spacer fabric of the aspirant channel may extend beyond the orifice in the top layer, advantageously reducing the possibility of occlusion of the orifice 352. In such an embodiment, the distal end of the fluidic connector has a distally facing opening to transmit negative pressure to the wound.

Figure 6:
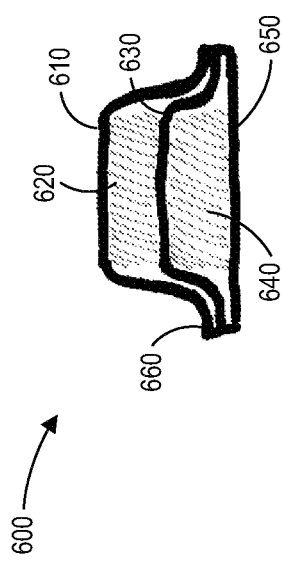
FIG. 6 illustrates a cross sectional view of an embodiment of a fluidic connector for irrigation and aspiration of wounds having a flat lower layer.

FIG. 6 illustrates a cross sectional view of the elongated length of an embodiment of a fluidic connector 600 having a substantially flat lower film layer 650, a lower spacer layer 640, an intermediate film layer 630, an upper spacer layer 620, and an upper film layer 610. The upper and intermediate film layers 610, 630 are sealed together or welded along a perimeter 660 such that the intermediate film layer 630 is slightly larger than the lower film layer 650 to accommodate the height of lower spacer layer 640, and the upper film layer 610 is slightly larger than the intermediate film layer 630 to accommodate the heights of both spacer layers as well as the height of the intermediate layer.

Figure 7:
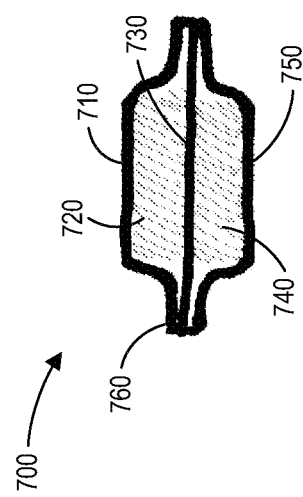
FIG. 7 illustrates an embodiment of a fluidic connector for irrigation and aspiration of wounds having the layers sealed in the middle of the height of the fluidic connector.

FIG. 7 illustrates a cross sectional view of the elongated length of an embodiment of a fluidic connector 700 having a lower film layer 750, a lower spacer layer 740, a substantially flat intermediate film layer 730, an upper spacer layer 720, and an upper film layer 710. The upper and intermediate film layers 710, 730 are sealed together or welded along a perimeter 760 such that the upper film layer 710 is slightly larger than the intermediate film layer 750 to accommodate the height of the upper spacer layer 720. In a substantially symmetrical configuration, the lower and intermediate film layers 750, 730 are adhered along a perimeter 760 such that the lower film layer 750 is slightly larger than the intermediate film layer 750 to accommodate the height of the lower spacer layer 740.

Advantageously, in the embodiments of FIGS. 6 and 7, the corresponding layers of each of the upper and lower fluid passages have side portions along sides of the elongate spacer material that are parallel to and adhered to each other. This gives the fluidic connector a flatter cross-sectional profile that decreases in dimension towards both side edges to facilitate sealing of a drape over the fluidic connector. Because the spacer material between the corresponding layers is flexible, the fluidic connector is relatively soft, and is capable of conforming to the contours of a patient's skin.

FIGS. 8A-D illustrate various views of an embodiment of a fluidic connector 800 for irrigation and aspiration of wounds having side-by-side channels 802, 803. As shown in the partial cross-sectional view of FIG. 8A, a flexible drape 820 such as those discussed above may be substantially sealed to the healthy skin of a patient surrounding a wound bed 840. The wound bed 840 may contain a wound filler 830, such as foam or gauze or other suitable material. In contrast to some of the embodiments described above, the fluidic connector 800 may be secured over at least one opening or orifice 810 in drape 820 to provide the wound cavity 840 with irrigation and negative pressure. The orifice 810 may be pre-made in the drape, or may be made by the health practitioner. The fluidic connector 800 comprises an applicator portion 806 that may be secured over the orifice 810 in the drape 820, and a flexible, elongate bridge portion 801 to connect the drape to sources of negative pressure and irrigation fluid, as described below. The elongate bridge portion may optionally be sealed to the drape and/or skin surrounding the wound using a suitable adhesive.

FIG. 8B illustrates a cross-sectional view of the fluidic connector 800 taken along a portion of the elongate bridge portion 801. The fluidic connector 800 may comprise a top layer 814 and a bottom layer 815, which may comprise flexible, liquid impermeable flexible films, such as polyurethane. The top and bottom layers 814, 815 may be sealed around a perimeter 817 of the fluidic connector, for example by heat welding. Extending along at least a portion of the length of the fluidic connector is middle separation portion 816, which creates a right channel 803 and a left channel 802 in the sealed top and bottom layers. Though the middle separation 816 is depicted at the center of the width of the fluidic connector, thus creating two equally sized right and left channels, it will be appreciated that in some embodiments the middle separation may be located more to one side or the other, thereby creating a right and left channel of different sizes. In some embodiments, the middle separation 816 may be a weld between the top and bottom layers. In other embodiments, the middle separation may be a vertically-extending layer connected at its lower end to the bottom layer 815 and at its upper end to the top layer 814.

The right and left channels shown in FIG. 8B each contain an elongate spacer material 812, 813. In some embodiments these may be the same material, while in other embodiments they may comprise different materials. For example, in one embodiment the spacer material 813 of the left channel 802 may comprise 3D fabric for transmission of negative pressure and aspiration of exudate, while the spacer material 812 of the right channel 803 may comprise open celled foam for transmission of irrigation fluid. In other embodiments the left channel 802 may be used for irrigation and comprise foam as the spacer material 813, and the right channel 803 may be used for aspiration and comprise 3D fabric as the spacer material 812. Other suitable materials for the spacer material are described with respect to the previous embodiments above.

Figure 8D:
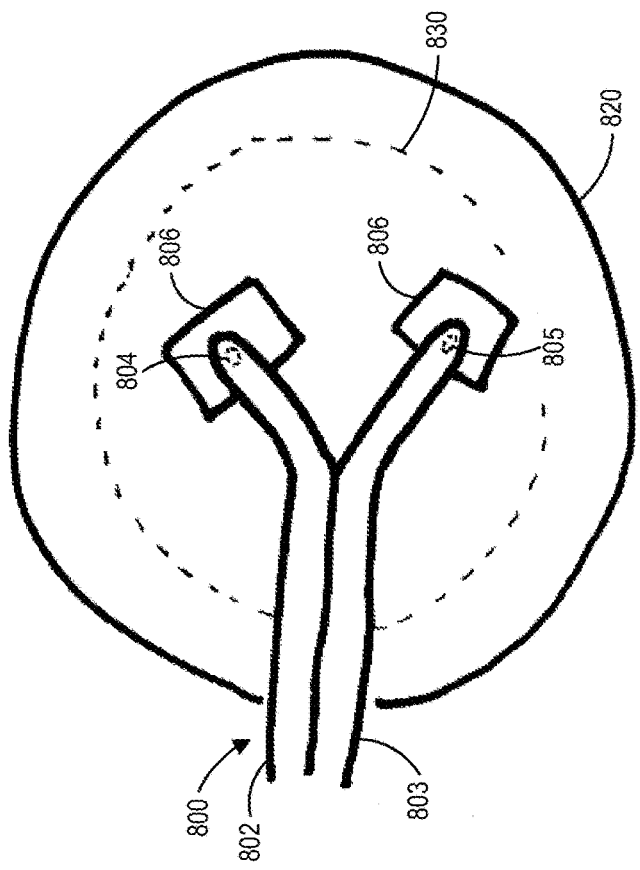
Figure 8C:
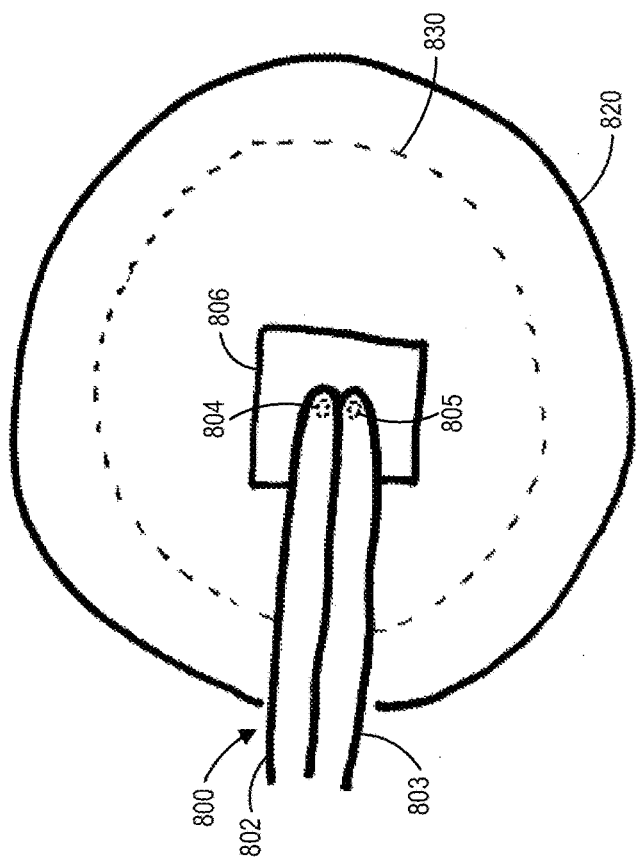

As illustrated in FIG. 8C, the side-by-side channels 802, 803 may be joined along a right side of the left channel 802 and a left side of the right channel 803 for the entire length of the fluidic connector 800. Some embodiments may form both channels out of two flexible film layers with a middle seal between the two layers used to separate the channels, for example a heat weld which runs down the center of the two layers as described above. The side-by-side channels 802, 803 may be connected to a single applicator flange portion 806. The applicator flange portion 806 may be secured to a lower surface of the distal end of the fluidic connector (e.g., secured to bottom layer 815), for example by heat welding or adhesive. In some embodiments, the applicator flange portion may merely be an extension of a lower layer (e.g., bottom layer 815) of the side-by-side channels 802, 803. The applicator flange portion 806 may be a layer of flexible film, and may have a pressure-sensitive adhesive provided on the lower surface thereof for sealing the fluidic connector 800 to a drape 820. In some embodiments, the adhesive layer may be protected prior to use by a removable protective layer (not illustrated) which may be peeled off to expose the adhesive. Each of the side-by-side channels 802, 803 may have an orifice 804, 805 located on the lower surface of a distal end thereof for delivery of fluid or aspiration through the at least one orifice 810 in the drape 820. The applicator flange portion 806 may have a hole or holes which correspond to the orifices 804, 805. In some embodiments, each of the channel orifices 804, 805 may be located over a separate orifice in the drape 820.

As illustrated by FIG. 8D, the side-by-side channels 802, 803 may be joined along a right side of the left channel 802 and a left side of the right channel 803 for only a portion of the length of the fluidic connector 800, and then may separate and connect to two separate applicator flange portions 806. Although the separated fluidic connector is depicted as a "Y" shape, it will be appreciated that many configurations are possible, for example one channel may remain straight while the other is bent. Some embodiments of the fluidic connector may be formed with a separated portion as illustrated, while some embodiments may be formed fully joined and may be separated as needed for use, for example by being pulled apart for the desired length.

One of the side-by-side channels 802, 803 may provide irrigation fluid to the wound. The other of the side-by-side channels 802, 803 may transmit negative pressure to the wound as well as aspirate fluid, which may comprise irrigation fluid and wound exudate, away from the wound. In some embodiments, the channels may be used simultaneously. In other embodiments, use of the channels may be alternated. For example, negative pressure may be provided to the wound cavity through the aspirant channel, and the wound may continue to receive negative pressure therapy for a first period of time. Irrigation fluid may then be provided to the wound through the irrigation channel and may be allowed to sit in the wound for a second period of time. After the second period of time, the aspirant channel may then be used to remove the irrigation fluid (and any wound exudate) and again initiate negative pressure in the wound cavity. This cycle may be repeated as needed, and it will be appreciated that although the example given began with a period of negative pressure, either negative pressure or irrigation may be used for the first cycle. This cyclic irrigation/aspiration process may be useful for bolus irrigation.

Additionally, some embodiments of the above-described aspiration and irrigation conduits may provide a means for venting air or a pressure monitoring line. For example, some embodiments may include a vent hole in the top layer of one of the two channels of the fluidic connector, for example at the proximal end of the elongate bridge. Other embodiments employ a third conduit or vent channel in the elongate bridge portion, the third conduit in fluid communication with a vent orifice. The vent orifice may be at the proximate end of the bridge portion, and may be provided with a filter. The vent channel may be provided with a spacer fabric, such as any of the spacer fabrics described above. Other embodiments may accomplish venting by means of a standalone vent port over a hole in the sealing drape.

In some embodiments, the third conduit or vent channel may be used as a separate pressure monitoring conduit. In other embodiments, the third conduit may be used to alternately vent and measure pressure. The conduit may switch between venting and pressure monitoring at regular intervals, or may switch in a controlled manner based on one or more parameters of the negative pressure system. In embodiments which alternate venting and pressure monitoring, air may be vented into to the wound for a first specified time period, for example via a valve attached to the third conduit; the valve may then be closed, thus preventing air from entering the negative pressure system and a pressure reading may be taken, for example via a pressure sensor fluidically attached to the third conduit. Once a stable pressure reading has been measured, or after a second specified period of time has passed, the valve may be opened and the cycle repeated. In some embodiments, the first specified time period may be 1-600 seconds, or approximately 1 to approximately 600 seconds, and the second specified time period may be 0.1-60 seconds, or approximately 0.1 second to approximately 60 seconds. Vent flows may be of the order 0.1 to 10 liters per minute, or approximately 0.1 to approximately 10 liters per minute. The addition of a vent may advantageously help to stabilize the pressure at the wound by minimizing the amount of liquid present in the main aspirant conduit and reducing the possibility of blockage formation.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A fluidic connector for providing at least aspiration to a wound site, comprising:
   an elongate bridge portion extending between a proximal end and a distal end and having an elongate length extending therebetween, the elongate bridge comprising a top layer, an intermediate layer and a bottom layer forming an upper fluid passage and a lower fluid passage;
   at least one applicator portion at the distal end of the elongate bridge portion; and
   a first conduit and a second conduit positioned side-by-side at the proximal end of the elongate bridge portion, wherein the top layer is positioned above the first and the second conduits, the intermediate layer is positioned underneath the first conduit and above the second conduit, and the bottom layer is positioned beneath the first conduit and the second conduit, and wherein the first conduit is in fluid communication with the upper fluid passage and the second conduit is in fluid communication with the lower fluid passage;
   wherein the intermediate layer does not pass above the first conduit or under the second conduit.

2. The fluidic connector of claim 1, wherein the top, intermediate, and bottom layers are formed from a flexible film material sealed to one another at a perimeter of the elongate bridge portion.

3. The fluidic connector of claim 1, wherein the top, intermediate, and bottom layers are formed from a liquid impermeable material.

4. The fluidic connector of claim 1, wherein at least the top layer is transparent.

5. The fluidic connector of claim 1, wherein the top layer, the intermediate layer, and the bottom layer each comprise an enlarged portion at a distal end thereof.

6. The fluidic connector of claim 1, wherein the top layer, the intermediate layer, and the bottom layer each comprise an enlarged, rounded or circular portion at a distal end thereof.

7. The fluidic connector of claim 1, wherein a lower surface of a portion of the bottom layer comprises an adhesive thereon for attaching to a manifold or for attaching to a skin surface surrounding the wound.

8. The fluidic connector of claim 1, further comprising a first spacer layer and a second spacer layer.

9. The fluidic connector of claim 1, further comprising a first spacer layer and a second spacer layer, wherein the first spacer layer is positioned between the top layer and the intermediate layer and the second spacer layer is positioned between the intermediate layer and the bottom layer.

10. The fluidic connector of claim 1, further comprising a first spacer layer and a second spacer layer, wherein the first spacer layer is configured to be used as an aspirant layer and the second spacer layer is configured to be used to transmit irrigation fluid.

11. The fluidic connector of claim 1, wherein the upper fluid passage and the lower fluid passage are separated at the distal end, each fluid passage being connected to a separate applicator portion.

12. The system of claim 1, further comprising a manifold in communication with the upper fluid passage or the lower fluid passage, the manifold being configured to provide irrigation fluid to the wound site, the manifold having a lower surface and being adapted to deliver irrigation fluid across a larger area than a distal end of the upper fluid passage or the lower fluid passage that the manifold is in communication with.

13. A system for treatment of a wound, comprising:
   a sealing membrane for covering the wound; and
   a fluidic connector according to claim 1 configured to be sealed over an opening in the sealing membrane.

14. The system of claim 1, further comprising a source of negative pressure configured to be in fluid communication with one of the fluid passages, and a source of irrigation fluid configured to be in fluid communication with the other of the fluid passages.

15. A system for treatment of a wound, comprising:
   a sealing membrane for covering the wound;
   a wound filler adapted to be positioned in the wound; and
   a fluidic connector according to claim 1 configured to be sealed over an opening in the sealing membrane.

16. The system of claim 15, further comprising a source of negative pressure configured to be in fluid communication with the upper fluid passage or the lower fluid passage and a source of irrigation fluid configured to be in fluid communication with the other of the upper and the lower fluid passages.

17. The system of claim 15, further comprising a waste collection canister configured to be in communication with the upper fluid passage or the lower fluid passage.

18. A system for treatment of a wound, comprising the fluidic connector of claim 1, a source of negative pressure configured to be in fluid communication with the upper fluid passage or the lower fluid passage and a source of irrigation fluid configured to be in fluid communication with the other of the upper fluid passage and the lower fluid passage.

19. The system of claim 18, further comprising a manifold configured for communication with the upper fluid passage or the lower fluid passage, the manifold comprising a plurality of radially extending arms.

20. The system of claim 19, wherein each of the plurality of radially extending arms comprises a plurality of irrigation orifices in the lower surface.

21. The system of claim 18, further comprising a waste collection canister configured to be in communication with the upper fluid passage or the lower fluid passage.

* * * * *